(12) United States Patent
Evans et al.

(10) Patent No.: US 8,870,941 B2
(45) Date of Patent: *Oct. 28, 2014

(54) GRAFT SYSTEMS HAVING FILLING STRUCTURES SUPPORTED BY SCAFFOLDS AND METHODS FOR THEIR USE

(75) Inventors: Michael A. Evans, Palo Alto, CA (US); Gwendolyn A. Watanabe, Sunnyvale, CA (US); Amy Lee, Sunnyvale, CA (US); Steven L. Herbowy, Palo Alto, CA (US)

(73) Assignee: Nellix, Irvine, CA (US)

( * ) Notice: Subject to any disclaimer, the term of this patent is extended or adjusted under 35 U.S.C. 154(b) by 37 days.

This patent is subject to a terminal disclaimer.

(21) Appl. No.: 13/285,897

(22) Filed: Oct. 31, 2011

(65) Prior Publication Data

US 2012/0046684 A1 Feb. 23, 2012

Related U.S. Application Data

(60) Division of application No. 11/413,460, filed on Apr. 28, 2006, now Pat. No. 8,048,145, which is a continuation-in-part of application No. 11/187,471, filed on Jul. 22, 2005, now Pat. No. 7,530,988.

(60) Provisional application No. 60/589,850, filed on Jul. 22, 2004, provisional application No. 60/675,158, filed on Apr. 28, 2005, provisional application No. 60/736,602, filed on Nov. 14, 2005.

(51) Int. Cl.
*A61F 2/06* (2013.01)
*A61F 2/07* (2013.01)
*A61F 2/90* (2013.01)
*A61F 2/95* (2013.01)

(52) U.S. Cl.
CPC ........... *A61F 2/07* (2013.01); *A61F 2230/0034* (2013.01); *A61F 2250/0069* (2013.01); *A61F 2002/077* (2013.01); *A61F 2250/0003* (2013.01); *A61F 2002/065* (2013.01); *A61F 2/90* (2013.01); *A61F 2/95* (2013.01)
USPC .......................... 623/1.16; 623/1.27; 623/1.35

(58) Field of Classification Search
USPC .......................... 606/191, 192, 194, 195, 200; 604/101.01–101.05; 623/1.25, 1.27, 623/1.32, 1.24, 1.35, 1.11, 1.16
See application file for complete search history.

(56) References Cited

U.S. PATENT DOCUMENTS

| 4,565,738 A | 1/1986 | Purdy |
| 4,638,803 A | 1/1987 | Rand |

(Continued)

FOREIGN PATENT DOCUMENTS

| DE | 4010975 A1 | 10/1991 |
| EP | 95302708.3 | 11/1995 |

(Continued)

OTHER PUBLICATIONS

Gilling-Smith, "Stent Graft Migration After Endovascular Aneurysm Repair," presented at 25th International Charing Cross Symposium, Apr. 13, 2003 [Power Point Presentation and Transcript], 56 pages total.

(Continued)

*Primary Examiner* — Julian W Woo
(74) *Attorney, Agent, or Firm* — Kilpatrick Townsend & Stockton LLP; Kenneth R. Shurtz, Esq.

(57) ABSTRACT

Aneurysms are treated by filling at least one double-walled filling structure with a curable medium within the aneurysm. The filling structures may be delivered over balloon deployment mechanisms in order to shape and open tubular lumens therethrough. Scaffolds are placed into the tubular lumens in order to help maintain the shape, anchor the filling structures in place, and provide improved blood flow transition into and out of the tubular lumens.

20 Claims, 22 Drawing Sheets

(56) References Cited

U.S. PATENT DOCUMENTS

| | | | |
|---|---|---|---|
| 4,641,653 A | 2/1987 | Rockey | |
| 4,704,126 A | 11/1987 | Baswell | |
| 4,710,192 A | 12/1987 | Liotta | |
| 4,728,328 A | 3/1988 | Hughes et al. | |
| 4,731,073 A | 3/1988 | Robinson | |
| 4,733,665 A | 3/1988 | Palmaz | |
| 4,743,258 A | 5/1988 | Ikada | |
| 4,763,654 A | 8/1988 | Jang | |
| 4,856,516 A | 8/1989 | Hillstead | |
| 4,858,264 A | 8/1989 | Reinhart | |
| 4,892,544 A | 1/1990 | Frisch | |
| 4,936,057 A | 6/1990 | Rhoades | |
| 4,976,692 A | 12/1990 | Atad | |
| 5,002,532 A | 3/1991 | Gaiser | |
| 5,074,845 A | 12/1991 | Miraki | |
| 5,104,404 A | 4/1992 | Wolff | |
| 5,108,417 A | 4/1992 | Sawyer | |
| 5,122,154 A | 6/1992 | Rhodes | |
| 5,133,732 A | 7/1992 | Wiktor | |
| 5,139,480 A | 8/1992 | Hickle | |
| 5,156,620 A | 10/1992 | Pigott | |
| 5,195,984 A | 3/1993 | Schatz | |
| 5,199,226 A | 4/1993 | Rose | |
| 5,217,484 A | 6/1993 | Marks | |
| 5,222,970 A | 6/1993 | Reeves | |
| 5,234,437 A | 8/1993 | Sepetka | |
| 5,242,399 A | 9/1993 | Lau | |
| 5,250,071 A | 10/1993 | Palermo | |
| 5,261,916 A | 11/1993 | Engelson | |
| 5,263,964 A | 11/1993 | Purdy | |
| 5,292,331 A | 3/1994 | Boneau | |
| 5,314,444 A | 5/1994 | Gianturco | |
| 5,316,023 A | 5/1994 | Palmaz et al. | |
| 5,330,528 A | 7/1994 | Lazim | |
| 5,334,217 A | 8/1994 | Das | |
| 5,350,397 A | 9/1994 | Palermo | |
| 5,352,199 A | 10/1994 | Tower | |
| 5,375,612 A | 12/1994 | Cottenceau | |
| 5,383,892 A | 1/1995 | Cardon | |
| 5,421,955 A | 6/1995 | Lau | |
| 5,423,849 A | 6/1995 | Engelson | |
| 5,425,739 A | 6/1995 | Jessen | |
| 5,425,744 A | 6/1995 | Fagan | |
| 5,441,510 A | 8/1995 | Simpson | |
| 5,441,515 A | 8/1995 | Khosravi | |
| 5,443,477 A | 8/1995 | Marin | |
| 5,443,496 A | 8/1995 | Schwartz | |
| 5,449,373 A | 9/1995 | Pinchasik | |
| 5,485,667 A | 1/1996 | Kleshinski | |
| 5,494,029 A | 2/1996 | Lane | |
| 5,496,277 A | 3/1996 | Termin | |
| 5,507,767 A | 4/1996 | Maeda | |
| 5,507,769 A | 4/1996 | Marin et al. | |
| 5,507,771 A | 4/1996 | Gianturco | |
| 5,514,115 A | 5/1996 | Frantzen | |
| 5,514,154 A | 5/1996 | Lau | |
| 5,522,882 A | 6/1996 | Gaterud | |
| 5,530,528 A | 6/1996 | Houki et al. | |
| 5,531,741 A | 7/1996 | Barbacci | |
| 5,534,024 A | 7/1996 | Rogers et al. | |
| 5,545,210 A | 8/1996 | Hess | |
| 5,549,662 A | 8/1996 | Fordenbacher | |
| 5,549,663 A | 8/1996 | Cottone, Jr. | |
| 5,554,181 A | 9/1996 | Das | |
| 5,562,641 A | 10/1996 | Flomenblit | |
| 5,562,698 A | 10/1996 | Parker | |
| 5,562,728 A | 10/1996 | Lazarus | |
| 5,569,295 A | 10/1996 | Lam | |
| 5,578,074 A | 11/1996 | Mirigian | |
| 5,578,149 A | 11/1996 | De Scheerder | |
| 5,591,195 A | 1/1997 | Taheri | |
| 5,591,223 A | 1/1997 | Lock | |
| 5,591,226 A | 1/1997 | Trerotola | |
| 5,591,228 A | 1/1997 | Edoga | |
| 5,591,230 A | 1/1997 | Horn | |
| 5,593,417 A | 1/1997 | Rhodes | |
| 5,601,600 A | 2/1997 | Ton | |
| 5,603,721 A | 2/1997 | Lau | |
| 5,605,530 A | 2/1997 | Fischell | |
| 5,607,442 A | 3/1997 | Fischell | |
| 5,607,445 A | 3/1997 | Summers | |
| 5,607,468 A | 3/1997 | Rogers | |
| 5,609,605 A | 3/1997 | Marshall | |
| 5,617,878 A | 4/1997 | Taheri | |
| 5,618,299 A | 4/1997 | Khosravi | |
| 5,624,411 A | 4/1997 | Tuch | |
| 5,630,840 A | 5/1997 | Mayer | |
| 5,632,760 A | 5/1997 | Sheiban | |
| 5,632,762 A | 5/1997 | Myler | |
| 5,632,763 A | 5/1997 | Glastra | |
| 5,632,771 A | 5/1997 | Boatman | |
| D380,266 S | 6/1997 | Boatman | |
| 5,634,941 A | 6/1997 | Winston | |
| 5,636,641 A | 6/1997 | Fariabi | |
| D380,831 S | 7/1997 | Kavteladze | |
| 5,662,614 A | 9/1997 | Edoga | |
| 5,665,117 A | 9/1997 | Rhodes | |
| 5,674,241 A | 10/1997 | Bley | |
| 5,676,697 A | 10/1997 | McDonald | |
| 5,683,449 A | 11/1997 | Marcade | |
| 5,690,643 A | 11/1997 | WiJay | |
| 5,693,038 A | 12/1997 | Suzuki et al. | |
| 5,693,067 A | 12/1997 | Purdy | |
| 5,693,088 A | 12/1997 | Lazarus | |
| 5,697,971 A | 12/1997 | Fischell | |
| 5,709,707 A | 1/1998 | Lock | |
| 5,718,713 A | 2/1998 | Frantzen | |
| 5,723,004 A | 3/1998 | Dereume | |
| 5,725,568 A | 3/1998 | Hastings | |
| 5,725,572 A | 3/1998 | Lam | |
| 5,728,068 A | 3/1998 | Leone | |
| 5,728,131 A | 3/1998 | Frantzen | |
| 5,728,158 A | 3/1998 | Lau | |
| 5,733,303 A | 3/1998 | Israel et al. | |
| 5,735,892 A | 4/1998 | Myers | |
| 5,735,893 A | 4/1998 | Lau | |
| 5,741,327 A | 4/1998 | Frantzen | |
| 5,741,333 A | 4/1998 | Frid | |
| 5,746,691 A | 5/1998 | Frantzen | |
| 5,755,769 A | 5/1998 | Richard | |
| 5,755,773 A | 5/1998 | Evans et al. | |
| 5,755,778 A | 5/1998 | Kleshinski | |
| 5,766,151 A | 6/1998 | Valley et al. | |
| 5,766,238 A | 6/1998 | Lau | |
| 5,769,882 A * | 6/1998 | Fogarty et al. | 128/898 |
| 5,776,114 A | 7/1998 | Frantzen | |
| 5,776,161 A | 7/1998 | Globerman | |
| 5,782,907 A | 7/1998 | Frantzen | |
| 5,785,679 A * | 7/1998 | Abolfathi et al. | 604/509 |
| 5,788,626 A | 8/1998 | Thompson | |
| 5,797,953 A | 8/1998 | Tekulve | |
| 5,800,393 A | 9/1998 | Sahota | |
| 5,800,512 A | 9/1998 | Lentz et al. | |
| 5,800,514 A | 9/1998 | Nunez | |
| 5,800,525 A | 9/1998 | Bachinski | |
| 5,807,404 A | 9/1998 | Richter | |
| 5,810,872 A | 9/1998 | Kanesaka | |
| 5,824,036 A | 10/1998 | Lauterjung | |
| 5,824,037 A | 10/1998 | Fogarty et al. | |
| 5,824,040 A | 10/1998 | Cox | |
| 5,824,049 A | 10/1998 | Ragheb | |
| 5,824,054 A | 10/1998 | Khosravi et al. | |
| 5,824,056 A | 10/1998 | Rosenberg | |
| 5,827,321 A | 10/1998 | Roubin | |
| 5,836,966 A | 11/1998 | St. Germain | |
| 5,843,160 A * | 12/1998 | Rhodes | 623/1.35 |
| 5,843,175 A | 12/1998 | Frantzen | |
| 5,846,246 A | 12/1998 | Dirks | |
| 5,846,261 A | 12/1998 | Kotula et al. | |
| 5,849,037 A | 12/1998 | Frid | |
| 5,860,998 A | 1/1999 | Robinson | |
| 5,863,627 A | 1/1999 | Szycher | |
| 5,867,762 A | 2/1999 | Rafferty et al. | |
| 5,868,685 A | 2/1999 | Powell et al. | |

(56) References Cited

U.S. PATENT DOCUMENTS

| | | |
|---|---|---|
| 5,868,708 A | 2/1999 | Hart |
| 5,868,782 A | 2/1999 | Frantzen |
| 5,871,537 A | 2/1999 | Holman |
| 5,873,907 A | 2/1999 | Frantzen |
| 5,876,448 A | 3/1999 | Thompson et al. |
| 5,879,381 A | 3/1999 | Moriuchi |
| 5,888,660 A | 3/1999 | Landoni et al. |
| 5,902,332 A * | 5/1999 | Schatz ............... 623/1.16 |
| 5,919,224 A | 7/1999 | Thompson |
| 5,928,279 A | 7/1999 | Shannon et al. |
| 5,931,866 A | 8/1999 | Frantzen |
| 5,944,750 A | 8/1999 | Tanner |
| 5,947,991 A | 9/1999 | Cowan |
| 5,948,184 A | 9/1999 | Frantzen |
| 5,976,178 A | 11/1999 | Goldsteen et al. |
| 5,984,955 A | 11/1999 | Wisselink |
| 5,994,750 A | 11/1999 | Yagi |
| 6,007,573 A | 12/1999 | Wallace |
| 6,015,431 A | 1/2000 | Thornton |
| 6,022,359 A | 2/2000 | Frantzen |
| 6,033,434 A | 3/2000 | Borghi |
| 6,042,606 A | 3/2000 | Frantzen |
| 6,056,776 A | 5/2000 | Lau |
| 6,066,167 A | 5/2000 | Lau |
| 6,066,168 A | 5/2000 | Lau |
| 6,083,259 A | 7/2000 | Frantzen |
| 6,093,199 A | 7/2000 | Brown |
| 6,099,548 A | 8/2000 | Taheri |
| 6,110,198 A | 8/2000 | Fogarty et al. |
| 6,123,715 A | 9/2000 | Amplatz |
| 6,123,722 A | 9/2000 | Fogarty |
| 6,124,523 A | 9/2000 | Banas et al. |
| 6,132,457 A | 10/2000 | Chobotov |
| 6,152,144 A | 11/2000 | Lesh |
| 6,152,943 A | 11/2000 | Sawhney |
| 6,168,592 B1 | 1/2001 | Kupiecki et al. |
| 6,187,033 B1 | 2/2001 | Schmitt |
| 6,187,034 B1 | 2/2001 | Frantzen |
| 6,190,402 B1 | 2/2001 | Horton et al. |
| 6,193,745 B1 | 2/2001 | Fogarty et al. |
| 6,196,230 B1 | 3/2001 | Hall et al. |
| 6,203,732 B1 | 3/2001 | Clubb |
| 6,214,022 B1 | 4/2001 | Taylor et al. |
| 6,231,562 B1 * | 5/2001 | Khosravi et al. ............. 604/507 |
| 6,235,050 B1 | 5/2001 | Quiachon et al. |
| 6,241,761 B1 | 6/2001 | Villafana |
| 6,254,633 B1 | 7/2001 | Pinchuk et al. |
| 6,261,305 B1 | 7/2001 | Marotta et al. |
| 6,280,466 B1 | 8/2001 | Kugler |
| 6,283,991 B1 | 9/2001 | Cox et al. |
| 6,290,722 B1 | 9/2001 | Wang |
| 6,290,731 B1 | 9/2001 | Solovay et al. |
| 6,293,960 B1 | 9/2001 | Ken |
| 6,296,603 B1 | 10/2001 | Turnlund et al. |
| 6,299,597 B1 | 10/2001 | Buscemi et al. |
| 6,299,604 B1 | 10/2001 | Ragheb |
| 6,312,462 B1 | 11/2001 | McDermott et al. |
| 6,312,463 B1 | 11/2001 | Rourke et al. |
| 6,325,816 B1 | 12/2001 | Fulton, III |
| 6,325,819 B1 | 12/2001 | Pavcnik et al. |
| 6,331,184 B1 | 12/2001 | Abrams |
| 6,331,191 B1 | 12/2001 | Chobotov |
| 6,334,869 B1 | 1/2002 | Leonhardt et al. |
| 6,344,056 B1 | 2/2002 | Dehdashtian |
| 6,375,675 B2 | 4/2002 | Dehdashtian et al. |
| 6,395,019 B2 | 5/2002 | Chobotov |
| 6,409,757 B1 | 6/2002 | Trout |
| 6,432,131 B1 | 8/2002 | Ravenscroft |
| 6,451,047 B2 | 9/2002 | McCrea |
| 6,463,317 B1 | 10/2002 | Kucharczyk et al. |
| 6,506,204 B2 | 1/2003 | Mazzocchi |
| 6,527,799 B2 | 3/2003 | Shanley |
| 6,544,276 B1 | 4/2003 | Azizi |
| 6,547,804 B2 | 4/2003 | Porter et al. |
| 6,554,858 B2 | 4/2003 | Dereume et al. |
| 6,576,007 B2 | 6/2003 | Dehdashtian et al. |
| 6,579,301 B1 | 6/2003 | Bales |
| 6,592,614 B2 | 7/2003 | Lenker et al. |
| 6,613,037 B2 | 9/2003 | Khosravi et al. |
| 6,645,242 B1 | 11/2003 | Quinn |
| 6,656,214 B1 | 12/2003 | Fogarty et al. |
| 6,656,220 B1 | 12/2003 | Gomez et al. |
| 6,663,607 B2 | 12/2003 | Slaikeu et al. |
| 6,663,667 B2 | 12/2003 | Dehdashtian et al. |
| 6,679,300 B1 | 1/2004 | Sommer et al. |
| 6,682,546 B2 | 1/2004 | Amplatz |
| 6,692,486 B2 | 2/2004 | Jaafar et al. |
| 6,695,833 B1 | 2/2004 | Frantzen |
| 6,729,356 B1 | 5/2004 | Baker et al. |
| 6,730,119 B1 | 5/2004 | Smalling |
| 6,733,521 B2 | 5/2004 | Chobotov |
| 6,761,733 B2 | 7/2004 | Chobotov |
| 6,773,454 B2 | 8/2004 | Wholey et al. |
| 6,776,771 B2 | 8/2004 | Van Moorlegem et al. |
| 6,827,735 B2 | 12/2004 | Greenberg |
| 6,843,803 B2 | 1/2005 | Ryan et al. |
| 6,878,161 B2 | 4/2005 | Lenker |
| 6,878,164 B2 | 4/2005 | Kujawski |
| 6,887,268 B2 | 5/2005 | Butaric et al. |
| 6,918,926 B2 | 7/2005 | Letort |
| 6,945,989 B1 | 9/2005 | Betelia et al. |
| 6,958,051 B2 | 10/2005 | Hart et al. |
| 6,960,227 B2 | 11/2005 | Jones et al. |
| 7,022,100 B1 | 4/2006 | Aboul-Hosn et al. |
| 7,105,012 B2 * | 9/2006 | Trout, III ............... 623/1.11 |
| 7,112,217 B1 | 9/2006 | Kugler |
| 7,122,052 B2 | 10/2006 | Greenhalgh |
| 7,131,991 B2 | 11/2006 | Zarins et al. |
| 7,147,661 B2 | 12/2006 | Chobotov et al. |
| 7,175,651 B2 | 2/2007 | Kerr |
| 7,229,472 B2 | 6/2007 | DePalma et al. |
| 7,314,483 B2 | 1/2008 | Landau et al. |
| 7,326,237 B2 | 2/2008 | DePalma et al. |
| 7,435,253 B1 | 10/2008 | Hartley et al. |
| 7,530,988 B2 | 5/2009 | Evans et al. |
| 7,666,220 B2 | 2/2010 | Evans et al. |
| 7,682,383 B2 | 3/2010 | Robin |
| 7,708,773 B2 | 5/2010 | Pinchuk et al. |
| 7,790,273 B2 | 9/2010 | Lee et al. |
| 7,828,838 B2 | 11/2010 | Bolduc et al. |
| 7,951,448 B2 | 5/2011 | Lee et al. |
| 2001/0020184 A1 | 9/2001 | Dehdashtian et al. |
| 2001/0027337 A1 | 10/2001 | Di Caprio |
| 2001/0027338 A1 | 10/2001 | Greenberg |
| 2001/0044655 A1 | 11/2001 | Patnaik et al. |
| 2002/0019665 A1 | 2/2002 | Dehdashtian et al. |
| 2002/0026217 A1 | 2/2002 | Baker et al. |
| 2002/0045848 A1 | 4/2002 | Jaafar et al. |
| 2002/0045931 A1 | 4/2002 | Sogard et al. |
| 2002/0052643 A1 | 5/2002 | Wholey et al. |
| 2002/0077594 A1 | 6/2002 | Chien et al. |
| 2002/0151953 A1 | 10/2002 | Chobotov |
| 2002/0151956 A1 | 10/2002 | Chobotov |
| 2002/0151958 A1 | 10/2002 | Chuter |
| 2002/0156518 A1 | 10/2002 | Tehrani |
| 2002/0165521 A1 | 11/2002 | Cioanta et al. |
| 2002/0169497 A1 | 11/2002 | Wholey et al. |
| 2002/0183629 A1 | 12/2002 | Fitz |
| 2003/0004560 A1 | 1/2003 | Chobotov |
| 2003/0009132 A1 | 1/2003 | Schwartz et al. |
| 2003/0014075 A1 | 1/2003 | Rosenbluth et al. |
| 2003/0028209 A1 | 2/2003 | Teoh et al. |
| 2003/0036745 A1 | 2/2003 | Khosravi et al. |
| 2003/0051735 A1 | 3/2003 | Pavcnik et al. |
| 2003/0074056 A1 | 4/2003 | Killion et al. |
| 2003/0078647 A1 | 4/2003 | Vallana et al. |
| 2003/0093145 A1 | 5/2003 | Lawrence-Brown et al. |
| 2003/0130720 A1 | 7/2003 | DePalma et al. |
| 2003/0130725 A1 | 7/2003 | DePalma et al. |
| 2003/0135269 A1 | 7/2003 | Swanstrom |
| 2003/0204242 A1 | 10/2003 | Zarins et al. |
| 2003/0204249 A1 | 10/2003 | Letort |
| 2003/0216802 A1 | 11/2003 | Chobotov et al. |
| 2003/0220649 A1 | 11/2003 | Bao et al. |

(56) References Cited

U.S. PATENT DOCUMENTS

| | | |
|---|---|---|
| 2003/0225446 A1 | 12/2003 | Hartley |
| 2004/0016997 A1 | 1/2004 | Ushio |
| 2004/0044358 A1 | 3/2004 | Khosravi et al. |
| 2004/0082989 A1 | 4/2004 | Cook et al. |
| 2004/0091543 A1 | 5/2004 | Bell et al. |
| 2004/0098096 A1 | 5/2004 | Eton |
| 2004/0116997 A1 | 6/2004 | Taylor et al. |
| 2004/0147811 A1 | 7/2004 | Diederich et al. |
| 2004/0153025 A1 | 8/2004 | Seifert et al. |
| 2004/0167607 A1 | 8/2004 | Frantzen |
| 2004/0193245 A1 | 9/2004 | Deem et al. |
| 2004/0204755 A1 | 10/2004 | Robin |
| 2004/0215172 A1 | 10/2004 | Chu et al. |
| 2004/0215316 A1 | 10/2004 | Smalling |
| 2004/0220522 A1 | 11/2004 | Briscoe et al. |
| 2004/0243057 A1 | 12/2004 | Vinten-Johansen et al. |
| 2005/0004660 A1 | 1/2005 | Rosenbluth et al. |
| 2005/0027238 A1 | 2/2005 | Fago et al. |
| 2005/0028484 A1 | 2/2005 | Littlewood |
| 2005/0065592 A1 | 3/2005 | Holzer |
| 2005/0090804 A1 | 4/2005 | Chobotov et al. |
| 2005/0096731 A1 | 5/2005 | Looi et al. |
| 2005/0215989 A1 | 9/2005 | Abboud et al. |
| 2005/0245891 A1 | 11/2005 | McCormick et al. |
| 2005/0251251 A1 | 11/2005 | Cribier |
| 2006/0015173 A1 | 1/2006 | Clifford et al. |
| 2006/0025853 A1 | 2/2006 | Evans et al. |
| 2006/0074481 A1* | 4/2006 | Vardi et al. ............... 623/1.36 |
| 2006/0135942 A1 | 6/2006 | Fernandes et al. |
| 2006/0142836 A1 | 6/2006 | Hartley et al. |
| 2006/0155369 A1 | 7/2006 | Edwin et al. |
| 2006/0161244 A1 | 7/2006 | Seguin |
| 2006/0184109 A1 | 8/2006 | Gobel |
| 2006/0206197 A1 | 9/2006 | Morsi |
| 2006/0212112 A1 | 9/2006 | Evans et al. |
| 2006/0265043 A1 | 11/2006 | Mandrusov et al. |
| 2006/0292206 A1 | 12/2006 | Kim et al. |
| 2007/0032850 A1 | 2/2007 | Ruiz et al. |
| 2007/0043420 A1 | 2/2007 | Lostetter |
| 2007/0050008 A1 | 3/2007 | Kim et al. |
| 2007/0055355 A1 | 3/2007 | Kim et al. |
| 2007/0061005 A1 | 3/2007 | Kim et al. |
| 2007/0150041 A1 | 6/2007 | Evans et al. |
| 2007/0162106 A1 | 7/2007 | Evans et al. |
| 2007/0162109 A1 | 7/2007 | Davila et al. |
| 2007/0208416 A1 | 9/2007 | Burpee et al. |
| 2007/0276477 A1 | 11/2007 | Lee et al. |
| 2008/0039923 A1 | 2/2008 | Taylor et al. |
| 2008/0154368 A1 | 6/2008 | Justis et al. |
| 2008/0228259 A1 | 9/2008 | Chu |
| 2008/0294237 A1 | 11/2008 | Chu |
| 2009/0099649 A1 | 4/2009 | Chobotov et al. |
| 2009/0198267 A1 | 8/2009 | Evans et al. |
| 2009/0209855 A1 | 8/2009 | Drilling et al. |
| 2009/0216125 A1 | 8/2009 | Lenker |
| 2009/0318949 A1* | 12/2009 | Ganpath et al. ............... 606/192 |
| 2009/0319029 A1 | 12/2009 | Evans et al. |
| 2010/0004728 A1 | 1/2010 | Rao et al. |
| 2010/0036360 A1* | 2/2010 | Herbowy et al. ............ 604/500 |
| 2010/0106087 A1* | 4/2010 | Evans et al. ............. 604/103.03 |
| 2010/0217383 A1 | 8/2010 | Leonhardt et al. |
| 2012/0016456 A1* | 1/2012 | Herbowy et al. ........... 623/1.11 |

FOREIGN PATENT DOCUMENTS

| | | |
|---|---|---|
| EP | 1325717 | 7/2003 |
| EP | 1903985 | 4/2008 |
| FR | 2834199 A1 | 7/2003 |
| JP | 4-322665 A | 11/1992 |
| JP | 2003/525692 | 9/2003 |
| JP | 2004-537353 A | 12/2004 |
| JP | 2005-505380 A | 2/2005 |
| JP | 2005-532120 A | 10/2005 |
| JP | 2008-510502 A | 4/2008 |
| WO | 97/17912 A1 | 5/1997 |
| WO | 97/19653 A1 | 6/1997 |
| WO | 98/53761 A1 | 12/1998 |
| WO | 99/00073 A1 | 1/1999 |
| WO | 99/44539 A2 | 9/1999 |
| WO | 00/29060 A2 | 5/2000 |
| WO | 00/51522 | 9/2000 |
| WO | 01/21108 | 3/2001 |
| WO | 01/66038 | 9/2001 |
| WO | 02/078569 A2 | 10/2002 |
| WO | 02/083038 A2 | 10/2002 |
| WO | 02/102282 | 12/2002 |
| WO | 03007785 A2 | 1/2003 |
| WO | 03/032869 A1 | 4/2003 |
| WO | 03/037222 A2 | 5/2003 |
| WO | 03/037222 A3 | 5/2003 |
| WO | 03/053288 A1 | 7/2003 |
| WO | 2004/004603 A1 | 1/2004 |
| WO | 2004/026183 A2 | 4/2004 |
| WO | 2004/026183 A3 | 4/2004 |
| WO | 2004/037116 A2 | 5/2004 |
| WO | 2004/037116 A3 | 5/2004 |
| WO | 2004/045393 A2 | 6/2004 |
| WO | 2006/012567 A2 | 2/2006 |
| WO | 2006/012567 A3 | 2/2006 |
| WO | 2006/116725 A2 | 11/2006 |
| WO | 2007/008600 A2 | 1/2007 |
| WO | 2007/142916 A2 | 12/2007 |

OTHER PUBLICATIONS

Donayre et al., "Fillable Endovascular Aneurysm Repair," Endovascular Today, pp. 64-66, Jan. 2009.

Carmi et al., "Endovascular stent-graft adapted to the endoluminal environment: prototype of a new endoluminal approach," J Endovasc Ther. Jun. 2002;9(3):380-381.

Extended European search report of corresponding EP Application No. 06751879.5, dated Apr. 16, 2013. 9 pages.

Patrick W. Serruys and Michael JB Kutryk; Handbook of Coronary Stents, Second Edition; 1998; pp. 45, 55, 78, 103, 112, 132, 158, 174, 185, 190, 207, 215, 230, 239; Martin Dunitz; UK.

Journal of Endovascular Therapy; Apr. 2000; pp. 111, 114, 132-140; vol. 7' No. 2; International Society of Endovascular Specialists; Phoenix, AZ.

International Search Report and Written Opinion of PCT Application No. PCT/US2009/046310, dated Jul. 29, 2009, 9 pages total.

International Search Report of PCT/US 06/16403, dated Aug. 7, 2007. 2 pages.

International Search Report and Written Opinion of PCT Application No. PCT/US2006/062257, mailed Jan. 18, 2008. 7 pages total.

International Search Report and Written Opinion of PCT Application No. PCT/US07/69671, dated Jul. 7, 2008, 9 pages.

International Search Report and Written Opinion of PCT Application No. PCT/US09/34136, D dated Apr. 8, 2009, 16 pages total.

U.S. Appl. No. 12/371,087, filed Feb. 13, 2009, first named inventor: K.T. Venkateswara Rao.

International Search Report and Written Opinion of PCT Application No. PCT/US09/41718, dated Jun. 22, 2009, 23 pages total.

Supplementary European Search Report and Search Opinion of EP Patent Application No. 05773726, mailed Apr. 23, 2010, 6 pages total.

International Search Report and the Written Opinion of the International Searching Authority, Issued in PCT/US2012/032612 on Jul. 25, 2012, 13 pages.

The International Search Report of the International Searching Authority for Application No. PCT/US2012/021878, mailed on May 23, 2012, 4 pages.

The Written Opinion, including the search, of the International Searching Authority for Application No. PCT/US2012/021878, mailed May 23, 2012, 9 pages.

European Search Report and Search Opinion of EP Patent Application No. 06774540.6, mailed Mar. 30, 2010, 6 pages total.

EP report, dated Nov. 7, 2013, of corresponding EP Application No. 09733719.0.

(56) References Cited

OTHER PUBLICATIONS

Search report dated Oct. 17, 2013 of corresponding PCT/US2012/032612.
International Preliminary Report on Patentability PCT/US2012/021878 dated Aug. 1, 2013.
Report of European Patent Application No. 06850439.8 dated May 15, 2013.
Report for European Patent Application No. 06850439.8, dated Aug. 8, 2012.
Examination report for JP Application. No. 2008-547709 dated Dec. 13, 2011.
International Search Report and Written Opinion of PCT Application No. PCT /US2009/046308, mailed Nov. 17, 2009, 12 pages total.
Examination Report of corresponding Japanese Application No. 2011-512667 dated Jun. 18, 2013.
International Preliminary Report on Patentability and Written Opinion of the International Searching Authority, Issued in PCT/US2010/061621 on Jul. 12, 2012, 7 pages.
PCT International Search Report and Written Opinion dated Feb. 28, 2011 for PCT Application No. PCT/US2010/61621. 11 pages.
U.S. Appl. No. 60/855,889, filed Oct. 31, 2006; first named inventor: Steven L. Herbowy.
U.S. Appl. No. 12/429,474, filed Apr. 24, 2009; first named inventor: Steven L. Herbowy.
U.S. Appl. No. 61/052,059, filed May 9, 2008; first named inventor: Gwendolyn A. Watanabe.
William Tanski, Mark Fillinger. *Outcomes of original and low-permeability Gore Excluder endoprosthesis for endovascular abdominal aortic aneurysm repair*. Journal of Vascular Surgery. Feb. 2007. p. 243-249.
Susan M. Trocciola et al. The development of endotension is associated with increased transmission of pressure and serous components in porous expanded polytetrafluoroethylene stent-grafts: Characterization using a canine model. Journal of Vascular Surgery. Jan. 2006. p. 109-116.
Shan-e-ali Haider et al. Sac behavior after aneurysm treatment with the Gore Excluder low-permeability aortic endoprosthesis: 12-month comparison to the original Excluder device. Journal of Vascular Surgery. vol. 44, No. 4. 694-700. Oct. 2006.
Examination report of EP Application No. 06751879.5, dated Mar. 24, 2014. 5 pages.
Examination Report of Japanese Patent Application No. 2007-522822, dated Feb. 8, 2011.
Examination Report of Japanese Patent Application No. 2011-506487, dated Jun. 11, 2013.
Official Action for Japanese Patent Application No. 2008-547709; dated Oct. 30, 2012.
Examination Report of Japanese Patent Application No. 2008-547709, dated Jul. 22, 2013.
Examination Report of European Patent Application 03754880.7; dated Dec. 16, 2010.
Examination Report of European Patent Application 03754880.7; dated Dec. 22, 2011.
Examination Report of European App. 03754880.7, dated Feb. 22, 2013.
Examination Report of European Application No. 03754880.7; dated Jun. 29, 2012. 4 pages.
Extended European Search Report of Application No. 11180827.5, dated Jan. 30, 2012. 6 pages.
Search report of corresponding PCT/US2014/021928, mailed May 20, 2014. 8 pages.
Examination Report of Japanese Patent Application No. 2011-506487, dated May 7, 2014.

\* cited by examiner

GRAFT SYSTEMS HAVING FILLING STRUCTURES SUPPORTED BY SCAFFOLDS AND METHODS FOR THEIR USE

CROSS-REFERENCES TO RELATED APPLICATIONS

The present application is a Divisional of U.S. application Ser. No. 11/413,460 filed Apr. 28, 2006 (now U.S. Pat. No. 8,048,145); which application is a continuation-in-part of U.S. Pat. No. 11/187,471filed on Jul. 22, 2005 (now U.S. Pat. No. 7,530,988); which claimed the benefit of priority to Provisional Appln. No. 60/589,850 filed Jul. 22, 2004, the full disclosures of which are incorporated herein by reference. The present application also claims the benefit of priority to Provisional Appln. No. 60/675,158, filed on Apr. 28, 2005 and Appln. No. 60/736,602 filed Nov. 14, 2005. The full disclosures, all of which are incorporated herein by reference in their entirety, for all purposes.

BACKGROUND OF THE INVENTION

1. Field of the Invention

The present invention relates generally to medical apparatus and methods for treatment. More particularly, the present invention relates to expandable prosthesis and methods for treating abdominal and other aneurysms.

Aneurysms are enlargements or "bulges" in blood vessels which are often prone to rupture and which therefore present a serious risk to the patient. Aneurysms may occur in any blood vessel but are of particular concern when they occur in the cerebral vasculature or the patient's aorta.

The present invention is particularly concerned with aneurysms occurring in the aorta, particularly those referred to as aortic aneurysms. Abdominal aortic aneurysms (AAA's) are classified based on their location within the aorta as well as their shape and complexity. Aneurysms which are found below the renal arteries are referred to as infrarenal abdominal aortic aneurysms. Suprarenal abdominal aortic aneurysms occur above the renal arteries, while thoracic aortic aneurysms (TAA's) occur in the ascending, transverse, or descending part of the upper aorta.

Infrarenal aneurysms are the most common, representing about seventy percent (70%) of all aortic aneurysms. Suprarenal aneurysms are less common, representing about 20% of the aortic aneurysms. Thoracic aortic aneurysms are the least common and often the most difficult to treat. Most or all present endovascular systems are also too large (above 12 F) for percutaneous introduction.

The most common form of aneurysm is "fusiform," where the enlargement extends about the entire aortic circumference. Less commonly, the aneurysms may be characterized by a bulge on one side of the blood vessel attached at a narrow neck. Thoracic aortic aneurysms are often dissecting aneurysms caused by hemorrhagic separation in the aortic wall, usually within the medial layer. The most common treatment for each of these types and forms of aneurysm is open surgical repair. Open surgical repair is quite successful in patients who are otherwise reasonably healthy and free from significant co-morbidities. Such open surgical procedures are problematic, however, since access to the abdominal and thoracic aortas is difficult to obtain and because the aorta must be clamped off, placing significant strain on the patient's heart.

Over the past decade, endoluminal grafts have come into widespread use for the treatment of aortic aneurysm in patients who cannot undergo open surgical procedures. In general, endoluminal repairs access the aneurysm "endoluminally" through either or both iliac arteries in the groin. The grafts, which typically have been fabric or membrane tubes supported and attached by various stent structures, are then implanted, typically requiring several pieces or modules to be assembled in situ. Successful endoluminal procedures have a much shorter recovery period than open surgical procedures.

Present endoluminal aortic aneurysm repairs, however, suffer from a number of limitations. A significant number of endoluminal repair patients experience leakage at the proximal juncture (attachment point closest to the heart) within two years of the initial repair procedure. While such leaks can often be fixed by further endoluminal procedures, the need to have such follow-up treatments significantly increases cost and is certainly undesirable for the patient. A less common but more serious problem has been graft migration. In instances where the graft migrates or slips from its intended position, open surgical repair is required. This is a particular problem since the patients receiving the endoluminal grafts are often those who are not considered good candidates for open surgery. Further shortcomings of the present endoluminal graft systems relate to both deployment and configuration. The multiple component systems require additional time for introducing each piece and even more time for assembling the pieces in situ. Such techniques are not only more time consuming, they are also more technically challenging, increasing the risk of failure. Current devices are also unsuitable for treating many geometrically complex aneurysms, particularly infrarenal aneurysms with little space between the renal arteries and the upper end of the aneurysm, referred to as short-neck or no-neck aneurysms. Aneurysms having torturous geometries, are also difficult to treat.

A particularly promising endoluminal graft is described in U.S. Publication No. 2006/0025853, which corresponds to parent application U.S. application Ser. No. 11/187,471, the full disclosure of which has previously been incorporated herein by reference. That patent application describes the treatment of the aortic and other aneurysms with a double-walled structure which is filled with a hardenable material which has cured in situ. The structure conforms to the shape of the aneurysmal space and resists migration and endoleaks. The particular design described, however, has certain shortcomings. For example, the lumen provided by the inner wall of the filled structure can sometimes deform so that the shape of the lumen is less than ideal. In other rare instances, leakage paths on the aortic or iliac ends of the graft may form.

For these reasons, it would desirable to provide improved methods, systems, and prosthesis for the endoluminal treatment of aortic aneurysms. Such improved methods, systems, and treatments should preferably provide implanted prosthesis which result in minimal or no endoleaks, resist migration, are relatively easy to deploy, have a low introduction profile (preferably below 12 F), and can treat most or all aneurismal configurations, including short-neck and no-neck aneurysms as well as those with highly irregular and asymmetric geometries. Further it would be desirable to provide fillable aneurysmal grafts having supported inner blood flow lumens and improved blood flow transitions at the aortic and/or iliac ends. At least some of these objectives will be met by the inventions described hereinafter.

2. Description of the Background Art

Grafts and endografts having fillable components are described in U.S. Pat. Nos. 4,641,653; 5,530,528; 5,665,117; and 5,769,882; U.S. Patent Publications 2004/0016997; and PCT Publications WO 00/51522 and WO 01/66038. The following patents and published applications describe stents and grafts having cuffs, extenders, liners, and related structures: U.S. Pat. Nos. 6,918,926; 6,843,803; 6,663,667; 6,656,214;

6,592,614; 6,409,757; 6,334,869; 6,283,991; 6,193,745; 6,110,198; 5,994,750; 5,876,448; 5,824,037; 5,769,882; 5,693,088; and 4,728,328; and U.S. Published Application Nos. 2005/0028484; 2005/0065592; 2004/0082989; 2004/0044358; 2003/0216802; 2003/0204249; 2003/0204242; 2003/0135269; 2003/0130725; and 2002/0052643.

BRIEF SUMMARY OF THE INVENTION

The present invention provides methods and systems for the endoluminal treatment of aneurysms, particularly aortic aneurysms including both abdominal aortic aneurysms (AAA's) and thoracic aortic aneurysms (TAA's). The systems include prostheses which comprise double-walled filling structures which are pre-shaped and otherwise adapted to substantially fill the enlarged volume of an aneurysm, particularly a fusiform aneurysm, leaving a lumen in place for blood flow.

The double-walled filling structures will thus usually have a generally toroidal structure with an outer wall, an inner wall, a potential space or volume between the outer and inner walls to be filled with a filling medium, and a generally tubular lumen inside of the inner wall which provides the blood flow lumen after the prosthesis has been deployed. The shape of the filling structure will be preferably adapted to conform to the aneurysm being treated. In some instances, the filling structure can be shaped for the aneurismal geometry of a particular patient using imaging and computer-aided design and fabrication techniques. In other instances, a family or collection of filling structures will be developed having different geometries and sizes so that a treating physician may select a specific filling structure to treat a particular patient based on the size and geometry of that patient's aneurysm. In all instances, the outer wall of the filling structure will conform or be conformable to the inner surface of the aneurysm being treated. While the inner wall of the structure will be aligned with lumens of the blood vessels on either side of the prosthesis after the prosthesis has been deployed.

The filling structures of the prosthesis will usually be formed from a non-compliant material, such as parylene, polyester (e.g., Dacron®), PET, PTFE, and/or a compliant material, such as silicone, polyurethane, latex, or combinations thereof. Usually, it will be preferred to form at least the outer wall partially or entirely from a non-compliant material to enhance conformance of the outer wall to the inner surface of the aneurysm. This is particularly true when the aneurysm has been individually designed and/or sized for the patient being treated.

The walls of the filling structures may consist of a single layer or may comprise multiple layers which are laminated, glued, heat bonded, ultrasonically bonded, or otherwise formed together. Different layers may comprise different materials, including both compliant and/or non-compliant materials. The structure walls may also be reinforced in various ways, including braid reinforcement layers, filament reinforcement layers, and the like.

In addition to the filling structures just described, the aneurysm treatment systems of the present invention will further include at least a first scaffold separate from the filling structure, where the scaffold can be expanded within the generally tubular lumen which provides the blood flow after the filling structure has been deployed in the aneurysm. The first scaffold will be adapted to expand within at least a first portion of the tubular lumen of the filling structure and may provide one or more specific advantages. For example, the scaffold may support and smooth the inside wall of the tubular lumen which in some cases might otherwise become uneven during hardening of the polymer fill. Scaffolds may also provide for anchoring of the filling structure, particularly at the aortic end of the graft when placed in an AAA. The scaffold may be partly or wholly covered with a membrane in order to form a graft. In such cases, the graft structure may help provide a transition from the blood vessel into the generally tubular lumen of the filling structure from the aortic end. Alternatively, the graft structure could provide one or a pair of transitions out of the iliac end of the filling structure. In a particular example, a graft structure can be used on either side of the filling structure in order to treat additional or continuing aneurysmal regions in the adjacent blood vessel.

The scaffolds used in combination with the double-walled filling structures of the present invention may take any form generally associated with a vascular or other luminal stents or grafts. For example, the scaffolds may be formed from an elastic material, particularly a spring steel or shape memory alloy, so that they may be delivered in a constrained configuration and allowed to expand in situ to anchor within the generally tubular lumen of the filling structure. Alternatively, the scaffold may be formed from a malleable metal or other material, such as stainless steel, and be delivered using a balloon catheter or other conventional stent expansion device. Grafts will usually comprise a metal frame covered in part or in whole by a membrane material, such as polyester, PTFE, or the like.

The geometry of the scaffold may also vary considerably. Often, the scaffold will extend over substantially the entire length of the inner wall of the generally tubular lumen of the filling structure. Frequently, the scaffold will extend outwardly from at least one of the ends of the generally tubular lumen into the adjacent blood vessel. The scaffold may also extend outwardly from both ends of the generally tubular lumen as well as covering the entire inner wall surface of that lumen.

In other instances, multiple scaffold structures may be provided within a single generally tubular lumen of the filling structure. In such cases, the two or more scaffolds may be adapted to be placed in series, frequently overlapping. In other instances, scaffolds may be adapted to be spaced apart at either or both ends and optionally at regions between the ends. In the case of covered scaffolds, the scaffold will typically comprise a metal frame, at least a portion of which is covered by a polymeric membrane or other covering. In other instances, however, the scaffold or portions thereof may be polymeric and optionally formed from a biodegradable polyester. It will frequently be desirable to cover the outside of the scaffold over at least those portions of the scaffold which engage the inner wall of the generally tubular lumen of the filling structure. The scaffolds and/or their covers may be coated with, impregnated with, or otherwise coupled to drugs or other bioactive substances for a variety of purposes, such as promoting tissue ingrowth, reducing thrombosis, reducing the risk of invention, and the like.

Preferred delivery protocols for the filling structures will utilize delivery catheters having a balloon or other expandable support for carrying the filling structure. When using balloons, the balloons will preferably be substantially or entirely non-compliant, although compliant and combination compliant/non-compliant balloons may also find use. The balloon or other mechanical expansion components of the delivery catheter will initially be disposed within the inner tubular lumen of the filling structure, with the filling structure generally being collapsed into a low width or low profile configuration over the expansion element. The delivery catheter may then be introduced intraluminally, typically into the iliac artery and upwardly to the region within the aorta to be treated. The delivery catheter will also include one or more lumens, tubes, or other components or structures for delivering the filling medium in a fluid form to an internal filling cavity of the filling structure. Thus, the delivery catheter can be used to both initially place and locate the filling structure of the prosthesis at the aneurismal site. Once at the aneurismal site, the internal tubular lumen of the structure can be expanded using the balloon or other expandable element on the delivery catheter. The filling structure itself will be filled and expanded by delivering the filling medium via the catheter into the internal volume of the filling structure. Both expansion and filling operations may be performed simultaneously, or can be performed in either order, i.e. the filling structure may be filled first with the delivery catheter balloon being expanded second, or vice versa. The filling structure(s) and/or delivery balloons may have radiopaque markers to facilitate placement and/or pressure sensors for monitoring filling and inflation pressures during deployment.

In preferred aspects of the present invention, the filling structure will be filled with a fluid (prior to hardening as described herein below) at a pressure which is lower than that of the expansion force provided by the delivery catheter, typically the filling pressure of the expandable balloon. Typically, the filling structure will be filled with filling medium at a pressure from 80 mm of Hg to 1000 mm of Hg, preferably from 200 mm of Hg to 600 mm of Hg, while the delivery balloon is inflated to a pressure in the range from 100 mm of Hg to 5000 mm of Hg, preferably from 400 mm of Hg to 1000 mm of Hg. These pressures are gage pressures, i.e. measured relative to atmospheric pressure.

As described thus far, in the present invention includes delivery of a single prosthesis and filling structure to an aneurysm. Delivery of a single filling structure will be particularly suitable for aneurysms which are remote from a vessel bifurcation so that both ends of the filling structure are in communication with only a single blood vessel lumen. In the case of aneurysms located adjacent a vessel bifurcation, such as the most common, infrarenal abdominal aortic aneurysms, it will often be preferable to utilize two such filling structures introduced in a generally adjacent, parallel fashion within the aneurismal volume. In the specific case of the infrarenal aneurysms, each prosthesis will usually be delivered separately, one through each of the two iliac arteries. After locating the filling structures of the prosthesis within the aneurismal space, they can be filled simultaneously or sequentially to fill and occupy the entire aneurismal volume, leaving a pair of blood flow lumens.

Suitable filling materials will be fluid initially to permit delivery through the delivery catheter and will be curable or otherwise hardenable so that, once in place, the filling structure can be given a final shape which will remain after the delivery catheter is removed. The fillable materials will usually be curable polymers which, after curing, will have a fixed shape with a shore hardness typically in the range from 10 durometer to 140 durometer. The polymers may be delivered as liquids, gels, foams, slurries, or the like. In some instances, the polymers may be epoxies or other curable two-part systems. In other instances, the polymer may comprise a single material which, when exposed to the vascular environment within the filling structure, changes state over time, typically from zero to ten minutes.

In a preferred aspect of the present invention, after curing, the filling material will have a specific gravity, typically in the range from 0.1 to 5, more typically from 0.8 to 1.2 which is generally the same as blood or thrombus. The filling material may also include bulking and other agents to modify density, viscosity, mechanical characteristics or the like, including microspheres, fibers, powders, gasses, radiopaque materials, drugs, and the like. Exemplary filling materials include polyurethanes, collagen, polyethylene glycols, microspheres, and the like.

The filling structures may be modified in a variety of other ways within the scope of the present invention. For example, the external surfaces of the filling structures may be partially or entirely modified to enhance placement within the aneurismal space, typically by promoting tissue ingrowth or mechanically interlocking with the inner surface of the aneurysm. Such surface modifications include surface roughening, surface stippling, surface flocking, fibers disposed over the surface, foam layers disposed over the surface, rings, and the like. It is also possible to provide biologically active substances over all or a portion of the external surface of the filling structure, such as thrombogenic substances, tissue growth promotants, biological adhesives, and the like. It would further be possible to provide synthetic adhesives, such as polyacrylamides, over the surface to enhance adherence.

In some instances, it will be desirable to modify all or a portion of the internal surface of the filling structure. Such surface modifications may comprise surface roughening, rings, stipples, flocking, foam layers, fibers, adhesives, and the like. The purpose of such surface modification will usually be to enhance the filling and bonding to the filling material, and to control the minimum wall thickness when the structure is filled particularly after the filling material has been cured. In particular instances, locations of the filling structure may be pressed together when the structure is deployed, thus potentially excluding filling material. In such instances, it will be desirable if the surfaces of the filling structure can adhere directly to each other.

In view of the above general descriptions of the present invention, the following specific embodiments may be better understood. In a first specific embodiment, methods for treating an aneurysm comprise positioning at least one double-walled filling structure across the aneurysm. By "across" the aneurysms, it is meant generally that the filling structure will extend axially from one anatomical location which has been identified by imaging or otherwise as the beginning of the aneurysm to a space-part location (or locations in the case of bifurcated aneurysm) where it has been established that the aneurysm ends. After positioning, the at least one filling structure is filled with a fluid filling medium so that an outer wall of the structure conforms to the inside of the aneurysm and an inner wall of the structure forms a generally tubular lumen to provide for blood flow after the filling structure has been deployed. While the filling structure is being filled, after the filling structure has been filled, or during both periods, the tubular lumen will preferably be supported, typically by a balloon or mechanically expansible element. After the filling structure has been filled, the filling material or medium is hardened while the tubular lumen remains supported. Supporting the tubular lumen during hardening assures that the lumen will have a desired geometry, will properly align with adjacent vascular lumens and that the tubular lumen being formed remains aligned with the native aortic and/or iliac artery lumens after the prosthesis has been fully implanted. Preferably, the support will be provided by a balloon which extends proximally and distally of the filling structure where the balloon may slightly "overexpand" in order to assure the desired smooth transition and conformance of the tubular lumen provided by the filling structure with the native vessel lumens.

After hardening, the support will be removed, leaving the filling structure in place. In some instances, however, prior to hardening, it will be desirable to confirm proper placement of the filling structure. This can be done using imaging techniques or otherwise testing for patency and continuity. In some instances, it may be desirable to first fill the filling structure with saline or other non-hardenable substance to make sure that the geometry of the filling structure is appropriate for the patient being treated. After testing, the saline may be removed and replaced with the hardenable filler.

In a second specific embodiment of the present invention, abdominal aortic aneurysms and other bifurcated aneurysms are treated by positioning first and second double-walled filling structures within the aneurismal volume. The first and second double-walled filling structures are positioned across the aneurysm, as defined above, extending from the aorta beneath the renal arteries to each of the iliac arteries, respectively. The first fluid filling structure is filled with a fluid filling material, the second filling structure is also filled with a fluid material, and the outer walls of each filling structure will conform to the inside surface of the aneurysm as well as to each other, thus providing a pair of tubular lumens for blood flow from the aorta to each of the iliac arteries. Preferably, the tubular lumens of each of the first and second filling structures are supported while they are being filled or after they have been filled. Further, the tubular lumens will preferably remain supported while the filling material is hardened, thus assuring that the transitions to the tubular lumens to the native vessel lumens remain properly aligned and conformed.

In a third specific embodiment of the present invention, systems for treating aneurysms comprise at least one double-walled filling structure and at least one delivery catheter having an expandable support positionable within a tubular lumen of the filling structure. The systems will usually further comprise a suitable hardenable or curable fluid filling medium. The particular characteristics of the filling structure and delivery balloon have been described above in connection with the methods of the present invention.

In a still further specific embodiment of the present invention, a system for treating abdominal aortic aneurysms comprises a first double-walled filling structure and a second double-walled filling structure. The first and second filling structures are adapted to be filled with a hardenable filling medium while they lie adjacent to each other within the aneurysm. The systems further comprise first and second delivery catheters which can be utilized for aligning each of the first and second filling structures properly with the right and left iliacs and the infrarenal aorta as they are being deployed, filled, and hardened.

The systems of the present invention for treating abdominal aortic aneurysms and other bifurcated lumens will typically include at least a first and a second scaffold, one for each of the tubular lumens defined by the first and second double-walled filling structures, respectively. The scaffolds will generally be the same as those described for the single filling structure embodiments, except that in some instances portions of the scaffold which extend into the adjacent blood vessel may be modified in order to enhance their ability to conform to each other. For example, the ends of the scaffolds may be modified to have D-shaped cross-sections so that when they are expanded, the flat surfaces of the D-shaped sections will engage each other to provide for a very full coverage of the area of the blood vessel. In other instances, the ends of the scaffolds which extend into the blood vessel may be formed into C-shaped structures which are expanded together to form a single generally continuous ring structure engaging the blood vessel wall.

BRIEF DESCRIPTION OF THE DRAWINGS

FIGS. 7H-1 and 7H-2 are cross-sectional views taken along line 7H-7H in FIG. 7H.

DETAILED DESCRIPTION OF THE INVENTION

Figure 1:
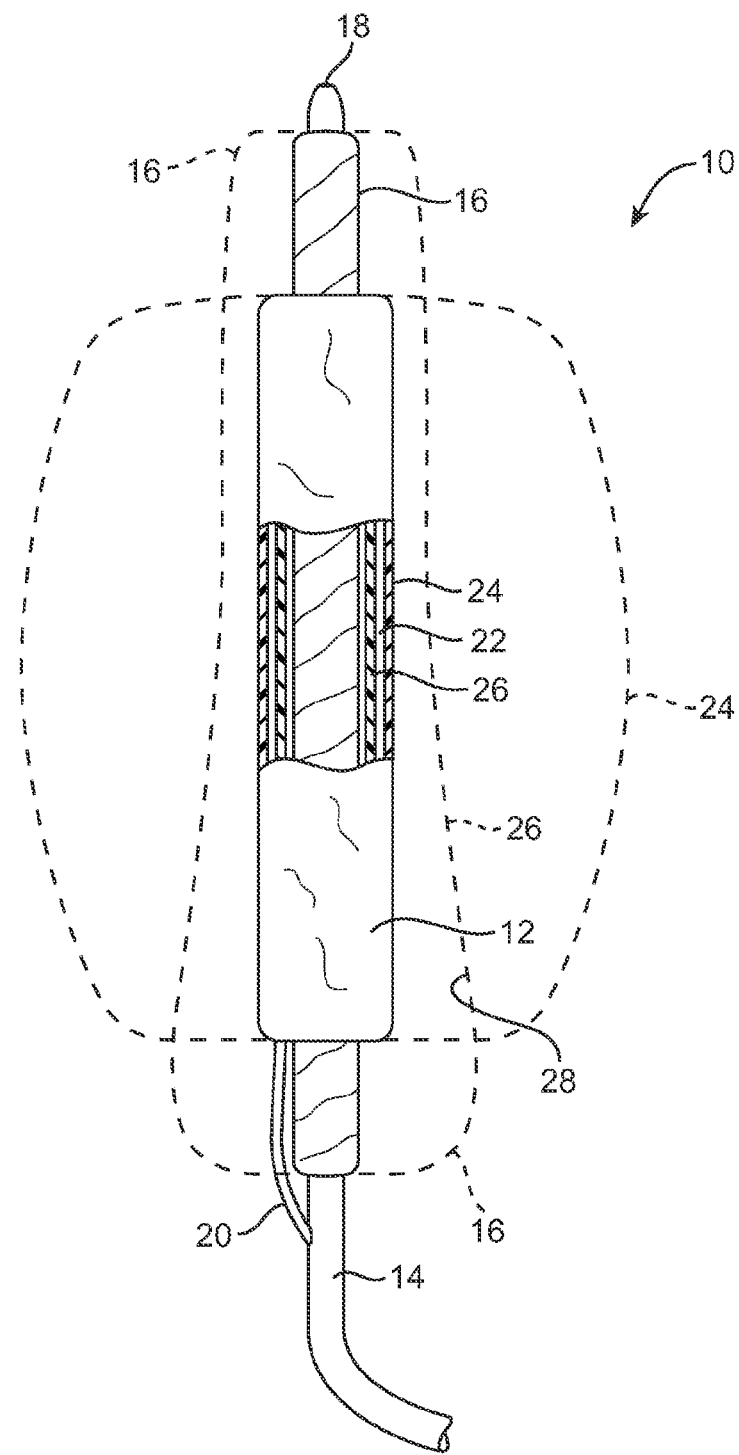
FIG. 1 illustrates a single prosthesis system comprising a filling structure mounted over a delivery catheter.

A system 10 constructed in accordance with the principles of the present invention for delivering a double-walled filling structure 12 to an aneurysm includes the filling structure and a delivery catheter 14 having an expandable element 16, typically an inflatable balloon, at its distal end. The catheter 14 will comprise a guidewire lumen 18, a balloon inflation lumen (not illustrated) or other structure for expanding other expandable components, and a filling tube 20 for delivering a filling medium or material to an internal space 22 of the double-walled filling structure 12. The internal space 22 is defined between an outer wall 24 and inner wall 26 of the filling structure. Upon inflation with the filling material or medium, the outer wall will expand radially outwardly, as shown in broken line, as will the inner wall 26, also shown in broken line. Expansion of the inner wall 26 defines an internal lumen 28. The expandable balloon or other structure 16 will be expandable to support an inner surface of the lumen 28, as also in broken line in FIG. 1.

Figure 2:
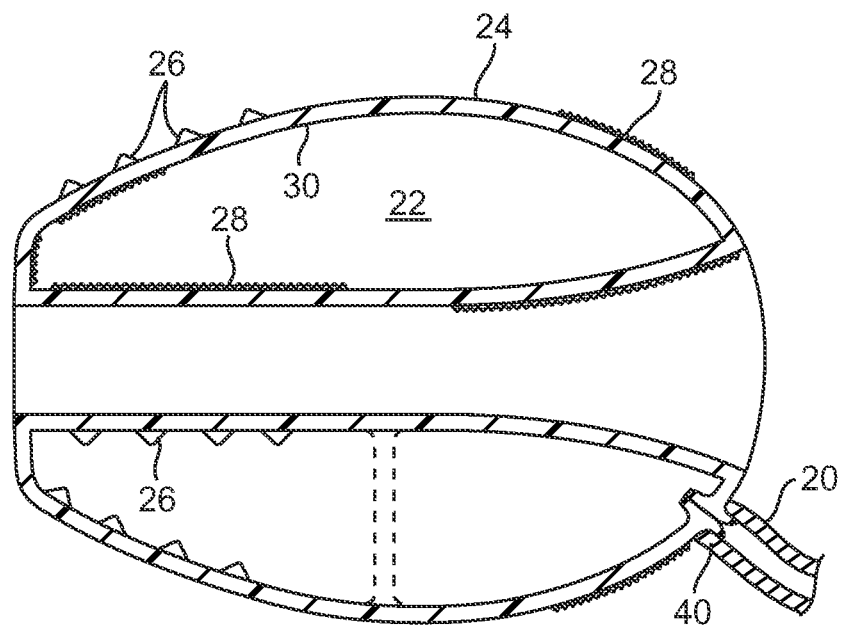
FIG. 2 is a cross-sectional view of the filling structure of FIG. 1 illustrating various surface modifications and a filling valve.

Referring now to FIG. 2, and the various internal and external surfaces may be shaped, coated, treated, or otherwise modified, to provide for a number of particular features in accordance with the principles of the present invention. For example, the outer wall 24 may be shaped to have rings, stipples, or other surface features which are typically formed into the material of the structure at the time of molding, vapor deposition, or other manufacturing process. The outer surface may also be coated with materials 28 which can be adhesives, drugs, active substances, fibers, flocking, foams, or a variety of other materials. In most cases, such surface features or modifications will be intended to enhance sealing or attachment of the outer wall 24 to the inner surface of the aneurysm being treated.

The inner surface 30 of the filling volume 22 may also be modified by providing features, coatings, surface roughening, or a variety of other modifications. The purpose of such internal features is typically to enhance adherence of the walls to the filling material or medium as the medium is cured or otherwise hardened. In some instances, materials may be coated on all or a portion of the inside surface 30 to induce or catalyze hardening of the filling material as it is being introduced.

The double-walled filling structure 12 will typically comprise at least one valve 40 to permit the introduction of the filling material or medium into the internal volume 22. As illustrated, the valve 40 may be a simple flap valve. Other more complex ball valves, and other one-way valve structures may be provided. In other instances, two-way valve structures may be provided to permit both filling and selective emptying of the internal volume 22. In other instances, the filling tube may comprise a needle or other filling structure to pass through the valve 40 to permit both filling and removal of filling medium.

Figure 3A:
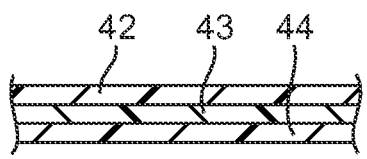
FIGS. 3A-3C illustrate alternative wall structures for the filling structure.
Figure 3B:
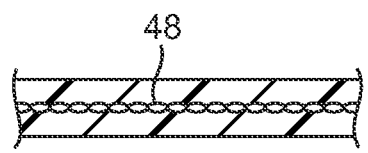
Figure 3C:
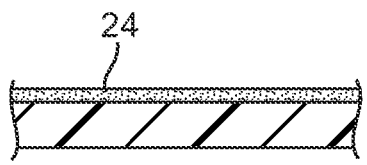

As illustrated in FIG. 2, the wall structure of the double-walled filling structure may be a single layer, typically molded or otherwise conventionally formed. The wall structures may also be more complex, as illustrated for example, FIGS. 3A-3C. FIG. 3A shows a multi-layered wall comprising layers 42, 43 and 44. It will be appreciated that such multiple layer structure can provide for increased strength, puncture resistance, variations in compliance and/or flexibility, differences in resistance to degradation, and the like. As shown in FIG. 3B, a single wall or multiple wall structure can be reinforced by braid, coils, or other metal or non-polymeric reinforcement layers or structures. As shown in FIG. 3C, the external surface 24 of the wall may be covered with drugs, fibers, protrusions, holes, active agents or other substances for a variety of purposes.

Figure 4:
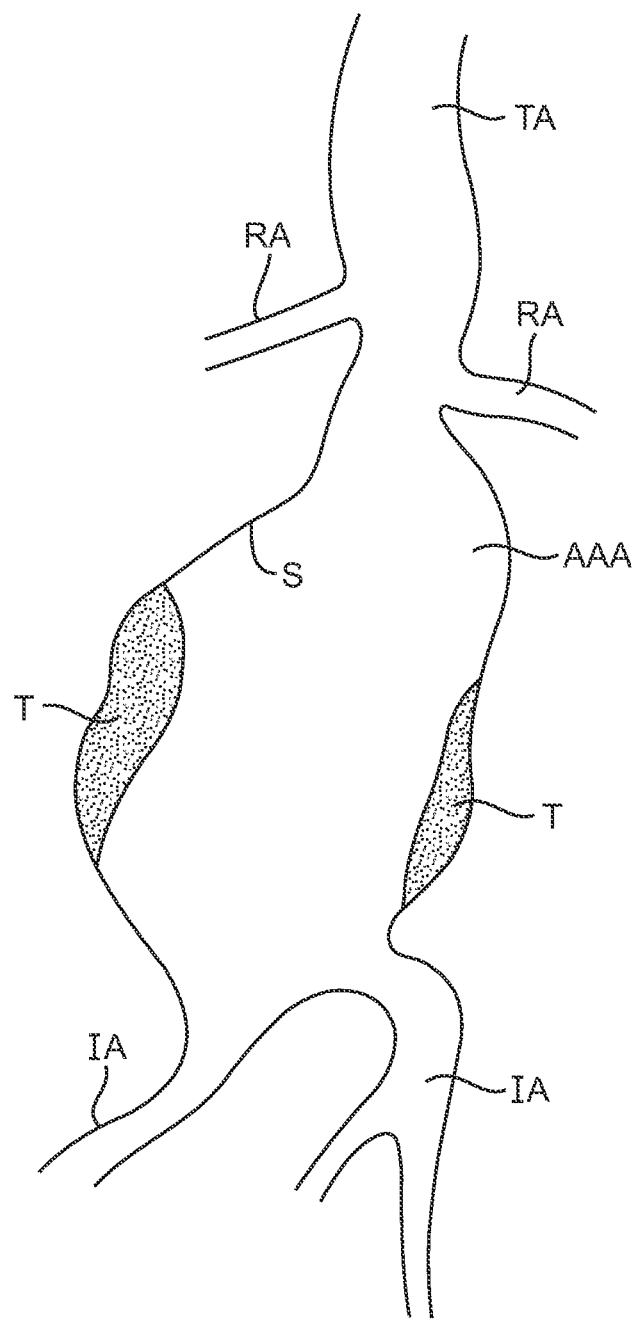
FIG. 4 illustrates the anatomy of an infrarenal abdominal aortic aneurysm.

Referring now to FIG. 4, the anatomy of an infrarenal abdominal aortic aneurysm comprises the thoracic aorta (TA) having renal arteries (RA) at its distal end above the iliac arteries (IA). The abdominal aortic aneurysm (AAA) typically forms between the renal arteries (RA) and the iliac arteries (IA) and may have regions of mural thrombus (T) over portions of its inner surface (S).

Figure 5A:
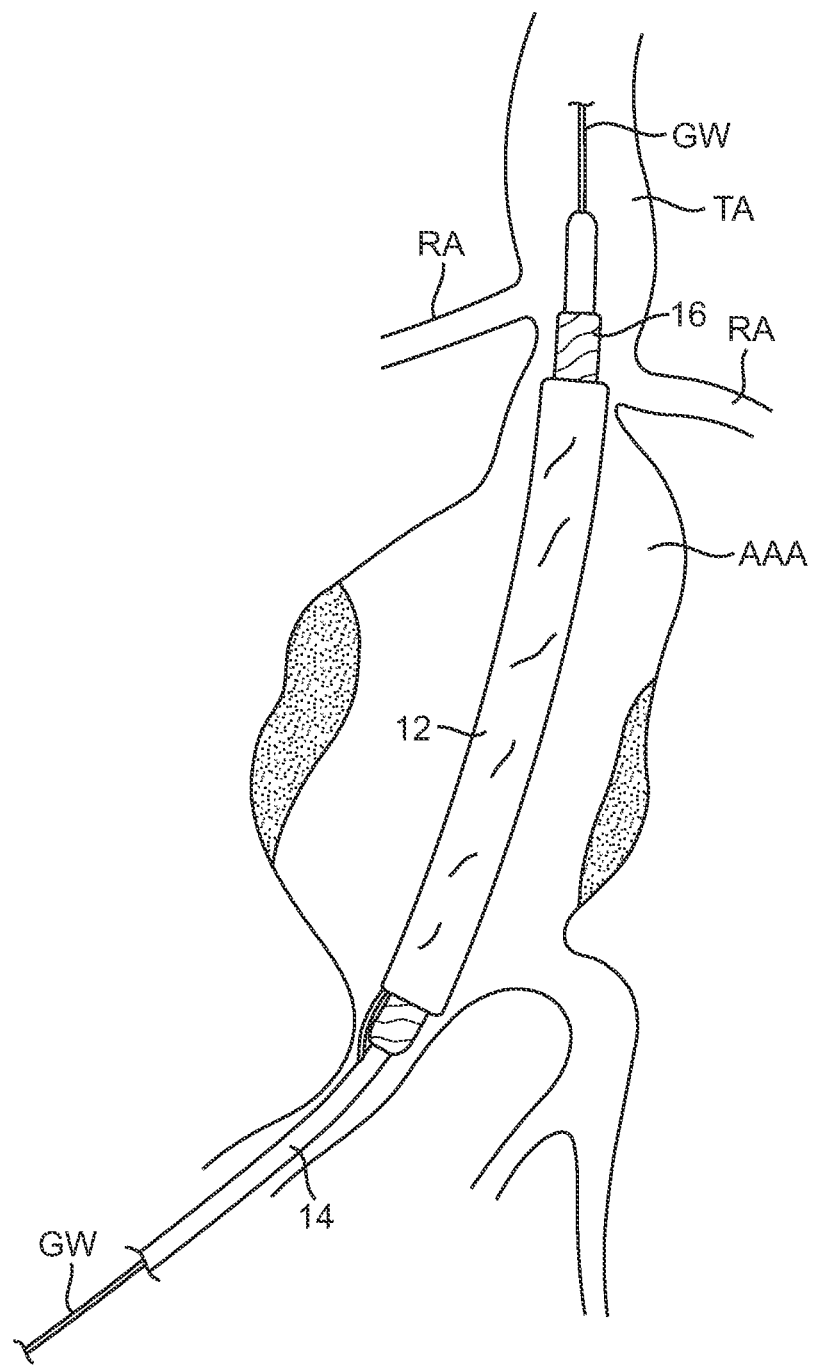
FIGS. 5A-5D illustrate use of the prosthesis system of FIG. 1 for treating the infrarenal abdominal aortic aneurysm.

Referring to FIGS. 5A-5D, the treatment system 10 of FIG. 1 may be utilized to treat the complex geometry of the transmural abdominal aortic aneurysm (AAA) of FIG. 4 by first positioning the delivery catheter 14 to place the double-walled filling structure 12 (in its unfilled configuration) generally across the aneurysm from the region of the aorta beneath the renal arteries (RA) to a region over the iliac arteries (IA), as best seen FIG. 5A. Usually, the delivery catheter 14 will be introduced over a guidewire (GW) through a puncture in the patient's groin accessing the iliac artery by the Seldinger technique.

After the double-walled filling structure 12 is properly positioned, a hardenable inflation medium is introduced into the internal space 22 filling of the inner space 22 expands the outer wall 24 of the structure outwardly so that it conforms to the inner surface (S) of the aneurismal space.

Figure 5B:
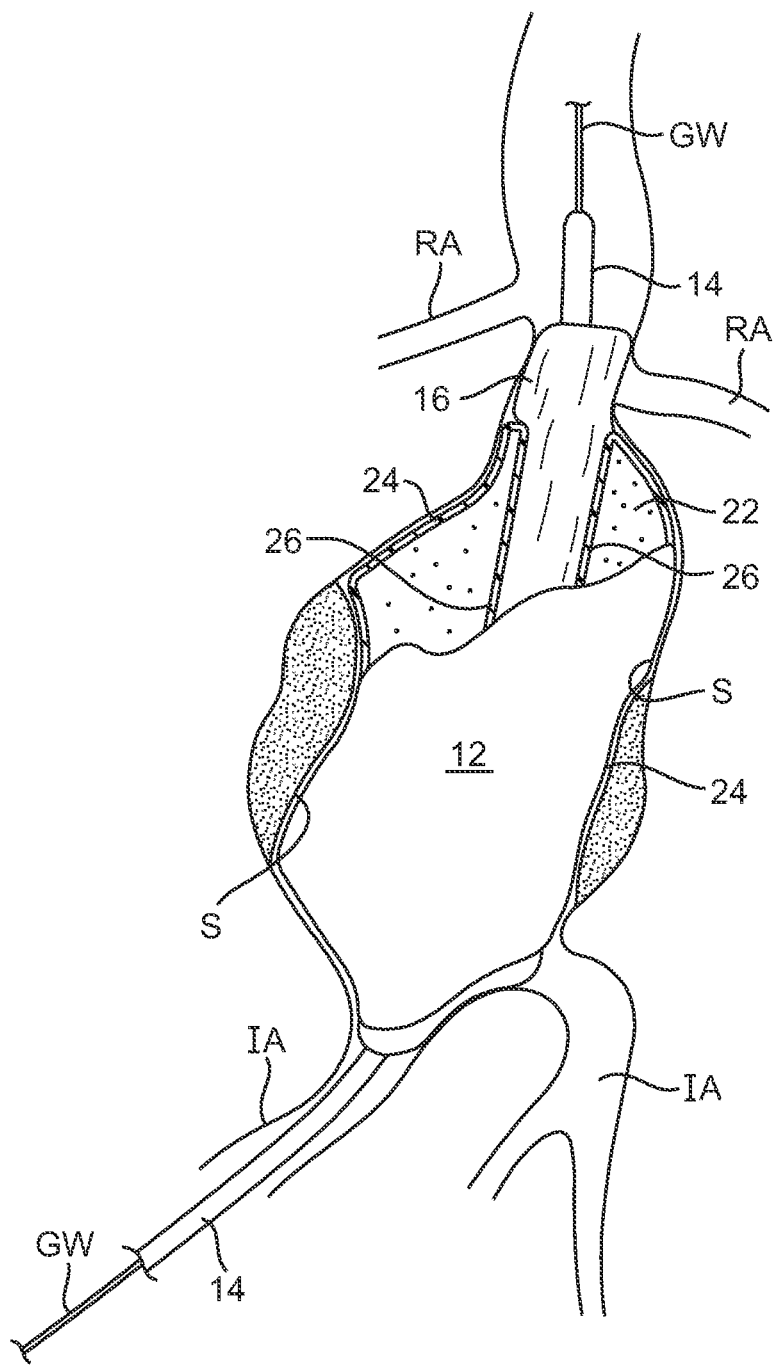
Figure 5C:
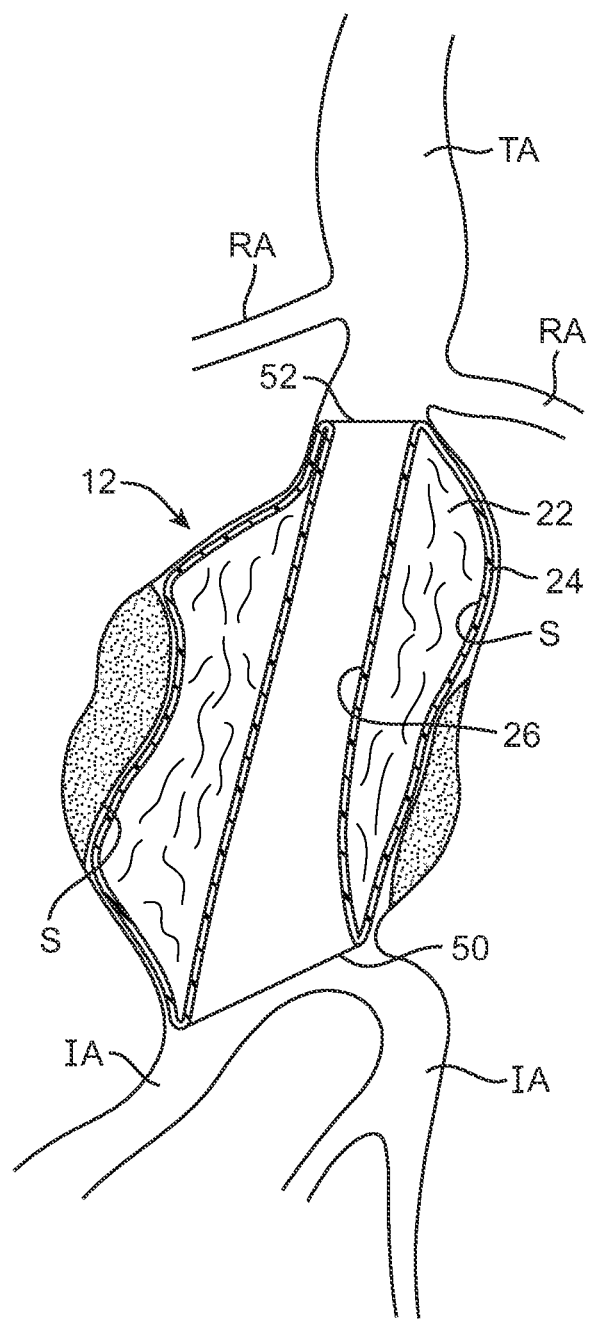

Before, during, or after filling of the double-walled filling structure 12 with inflation medium, as illustrated in FIG. 5B, the balloon 16 or other expansible structure will also be inflated or expanded to open the tubular lumen defined by the interior of the inner wall 26. In a preferred embodiment, the balloon 16 will be generally compliant, typically having a maximum diameter of width which is at or slightly larger than the desired tubular lumen diameter or width through the deployed filling structure 12. The filling structure 12, in contrast, may be partially or completely formed from a generally non-compliant material, thus allowing the non-compliant balloon or other expansible structure 16 to fully open the tubular lumen and conform the ends of the lumens to the aorta and iliac walls, as illustrated in FIG. 5C. A lower or proximal end 50 of the tubular lumen will be flared to a larger diameter so that it can accommodate the openings into both of the iliac arteries (IA) as illustrated. Thus, it will be preferred to utilize a filling structure 12 geometry which has been chosen or fabricated to match the particular patient geometry being treated. It will also be preferable to use a balloon 16 or other expansible structure which will be shaped to preferentially open the lower proximal end 50 of the tubular lumen to a larger diameter than the upper or distal end 52.

After the filling material has been introduced to the filling structure 12, typically through the filling tube 20, the fluid filling material must be cured or otherwise hardened to provide for the permanent implant having a generally fixed structure which will remain in place in the particular aneurismal geometry. Methods for curing or hardening the filling material will depend on the nature of the filling material. For example, certain polymers may be cured by the application of energy, such as heat energy or ultraviolet light. Other polymers may be cured when exposed to body temperature, oxygen, or other conditions which cause polymerization of the fluid filling material. Still others may be mixed immediately prior to use and simply cure after a fixed time, typically minutes.

Figure 5D:
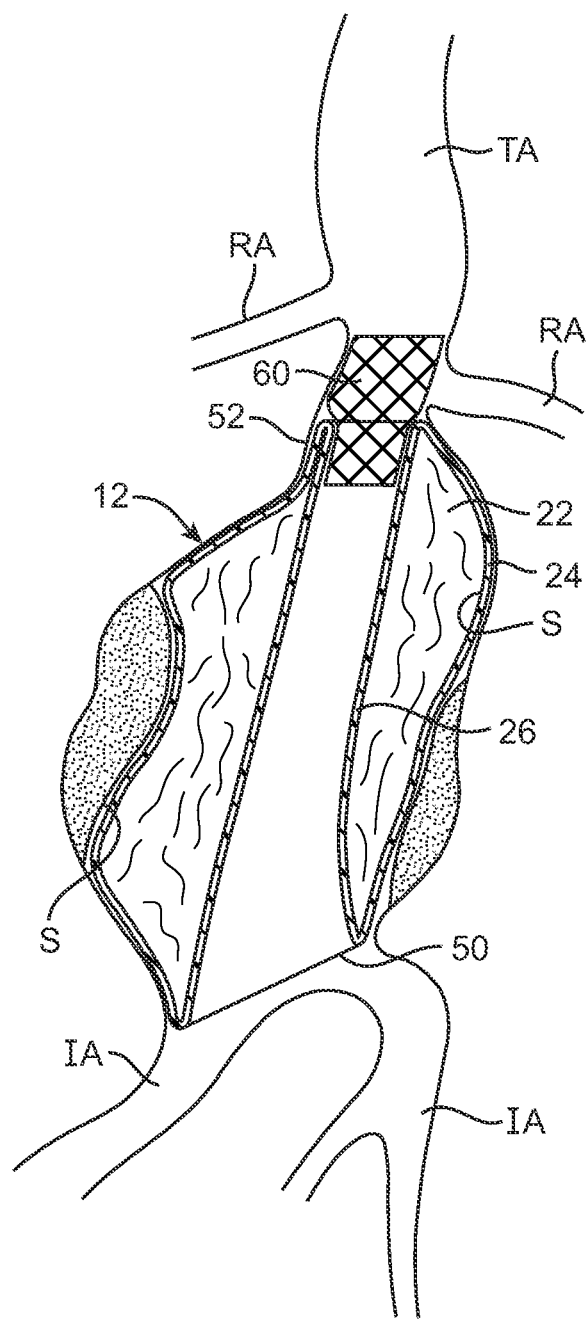

In accordance with the present invention, at least one scaffold will be placed into the tubular lumen defined by the inner wall 26. As illustrated in FIG. 5D, the scaffold may be a short, stent-like structure which may be implanted in the upper proximal opening 52 of the tubular lumen of the filling structure 12 in order to help anchor the upper end of the structure and prevent intrusion of blood into the region between the outer wall 24 and the inner surface S of the aneurysm and to generally improve the transition from the aorta into the tubular lumen. The stent-like structure 60 may comprise any conventional stent, graft, or other expandable luminal support structure known in the arts.

Figure 5E:
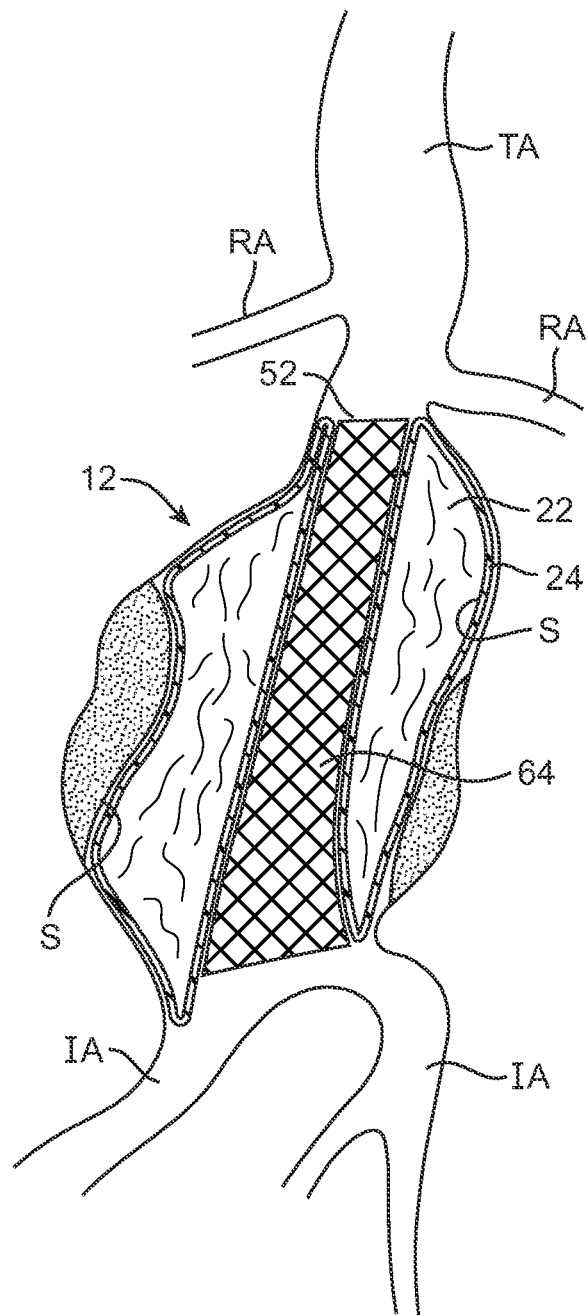
FIGS. 5E-5H illustrate the introduction of scaffolds into the tubular lumens of the filling structures of the systems of FIGS. 5A-5D.

As shown in FIG. 5E, an alternative stent structure 64 may span the entire length from the aortic end of the filling structure 12 to the iliac end. Stent structure 64 could also comprise any conventional stent or graft structure, typically being an expandable metal frame optionally covered with a membrane to form a graft.

Figure 5F:
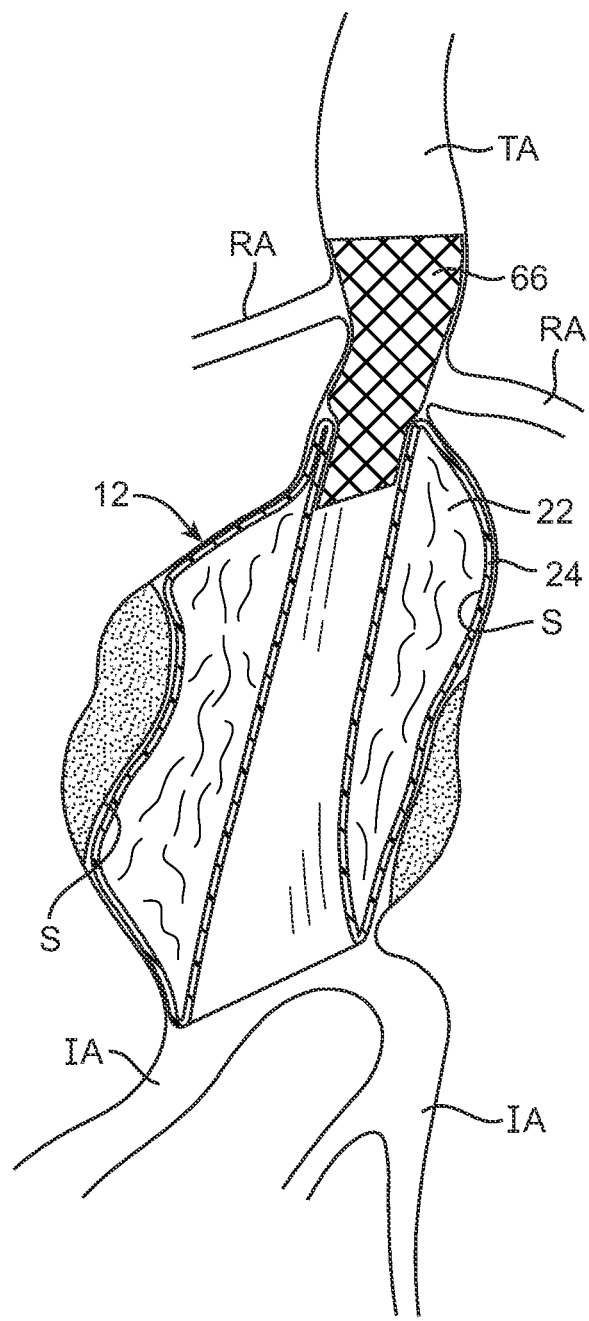

As shown in FIG. 5F, a further alternative stent structure 66 may extend fully through the filling structure and into the thoracic aorta TA, often covering the renal arteries RA. The portion of the stent 66 which extends through the filling structure 12 will often be covered with a membrane or other protective material so that the stent is actually a graft within the filling structure. A portion of the stent structure within the thoracic aorta TA, however, will preferably be left open to permit blood flow into the renal arteries RA.

Figure 5G:
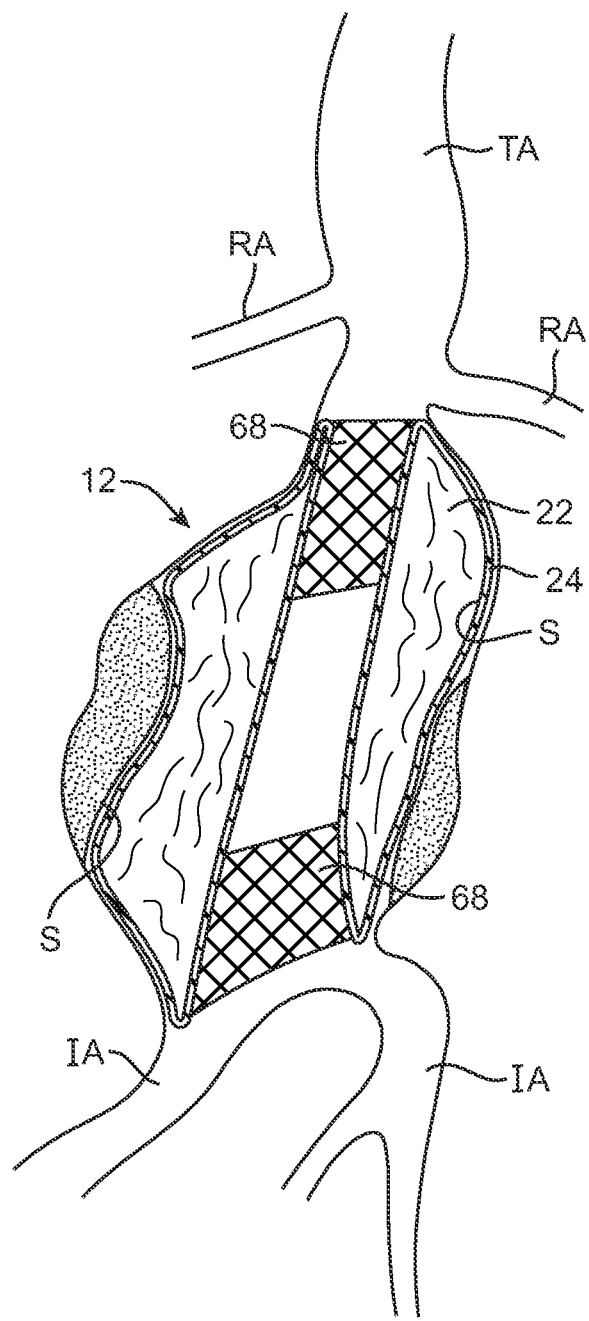

As shown in FIG. 5G, two or more stent structures 68 may be implanted within the tubular lumen of the filling structure 12. As illustrated, the relatively short stent structures 68 are positioned at the aortic side and the iliac side of the filling structure. They could be positioned elsewhere, and the stent segments could be longer and extend into either the aorta either or both of the iliacs.

Figure 5H:
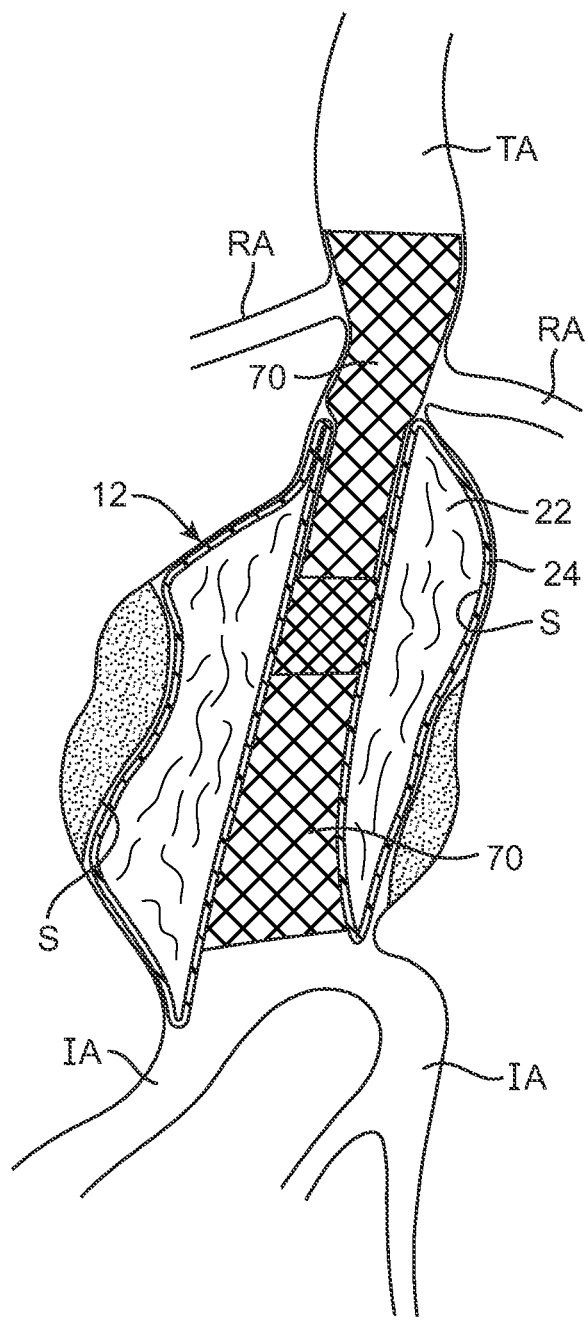

As shown in FIG. 5H, two or more stent structures 70 may be deployed within the tubular lumen of the filling structure 12 in an overlapping manner. By overlapping the stent segment 70, the overall length of the stent structure can be adjusted, e.g., to fully cover the renal arteries if that is desired, or in other instances to avoid covering the renal arteries if that is what is desired.

The stents, grafts, and other scaffold structures will often be delivered using separate delivery catheters (not shown) of the type commonly used to intravascularly deliver stents and grafts. The scaffold delivery catheters may comprise balloons or other expansion elements for expanding malleable scaffolds in situ. Alternatively, the delivery catheters could comprise tubular sheaths for covering and constraining self-expanding scaffolds prior to release within the tubular lumens of the filling structures. Systems could also deliver the scaffold(s) simultaneously with the filling structure(s), often on a common delivery catheter system.

Figure 6:
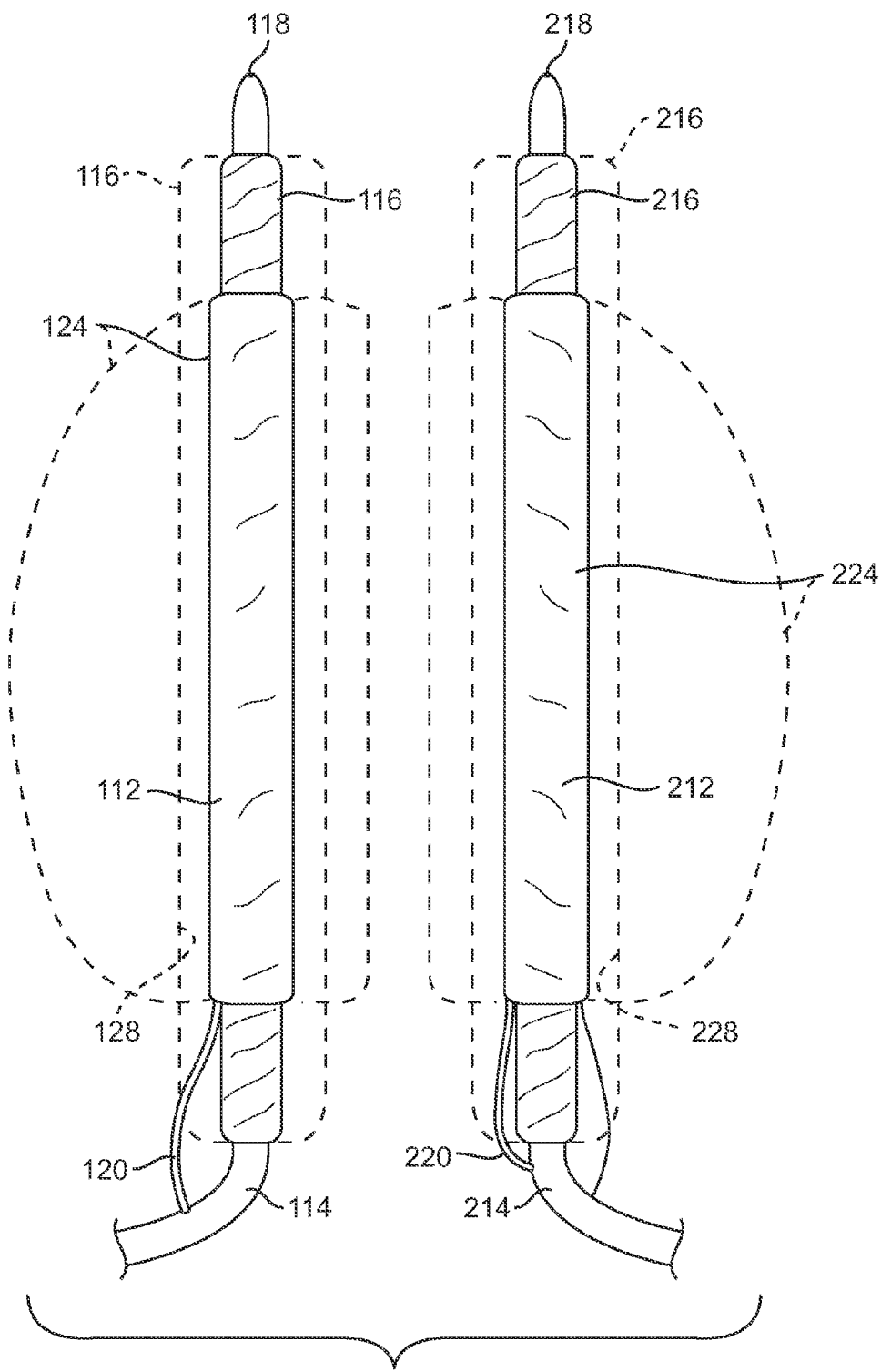
FIG. 6 illustrates a system in accordance with the principles of the present invention comprising a pair of prosthesis for delivery to an infrarenal abdominal aortic aneurysm, where each prosthesis comprises a filling structure mounted on a delivery catheter.

In a particular and preferred aspect of the present invention, a pair of double-walled filling structures will be used to treat infrarenal abdominal aortic aneurysms, instead of only a single filling structure as illustrated in FIGS. 5A-5C. A system comprising such a pair of filling structures is illustrated in FIG. 6 which includes a first filling structure 112 and a second filling structure 212. Each of the filling structures 112 and 212 are mounted on delivery catheters 114 and 214, respectively. The components of the filling structures 112 and 212 and delivery catheters 114 and 214 are generally the same as those described previously with respect to the single filling structure system 10 of FIG. 1. Corresponding parts of each of the fillings systems 112 and 212 will be given identical numbers with either the 100 base number or 200 base number. A principal difference between the filling structures 112 and 212, on the one hand, and the filling structure 12 of FIG. 1 is that the pair of filling structures will generally have asymmetric configurations which are meant to be positioned adjacent to each other within the aneurismal space and to in combination fill that space, as will be described with specific reference to FIG. 7A-7F below.

Figure 7A:
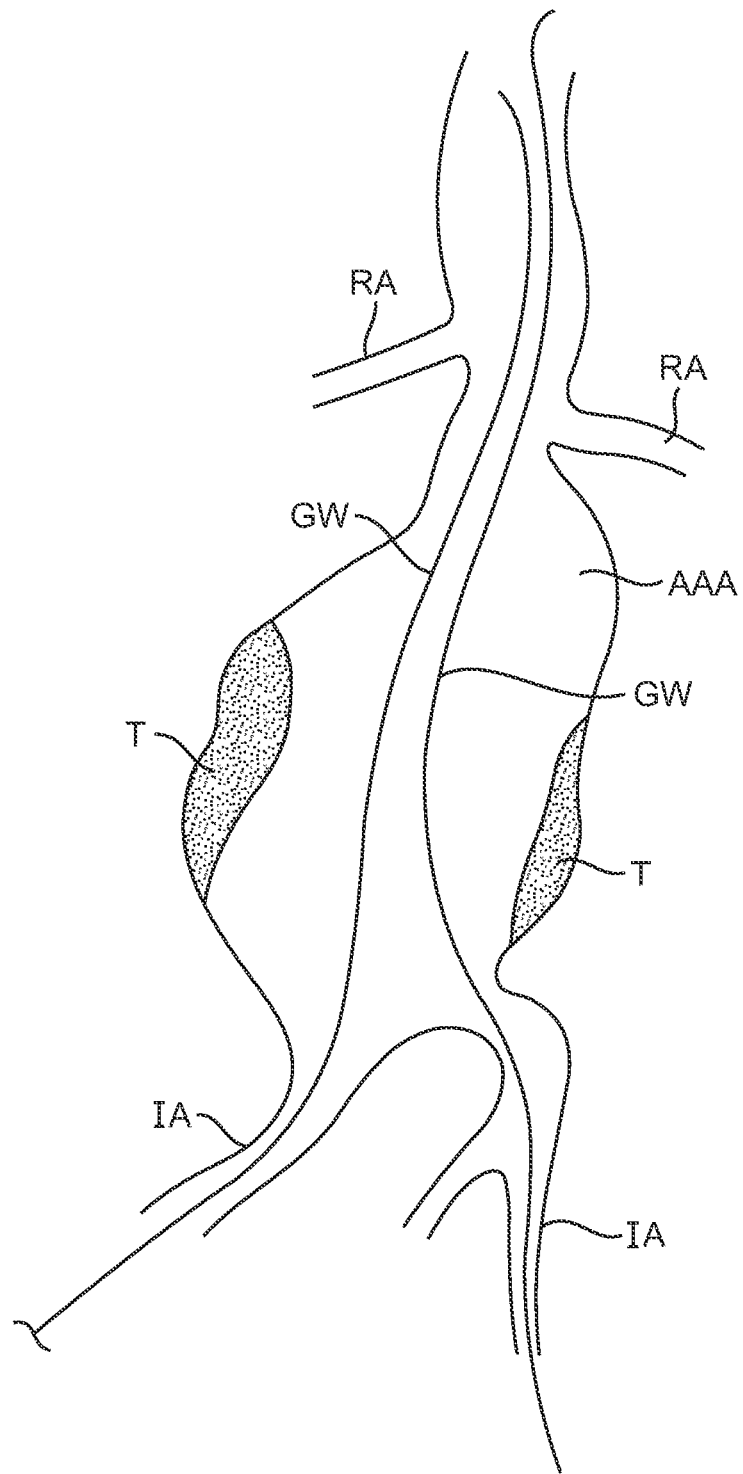
FIGS. 7A-7F illustrate use of the filling structures of the prosthesis system of FIG. 6 for treating an infrarenal abdominal aortic aneurysm.
Figure 7B:
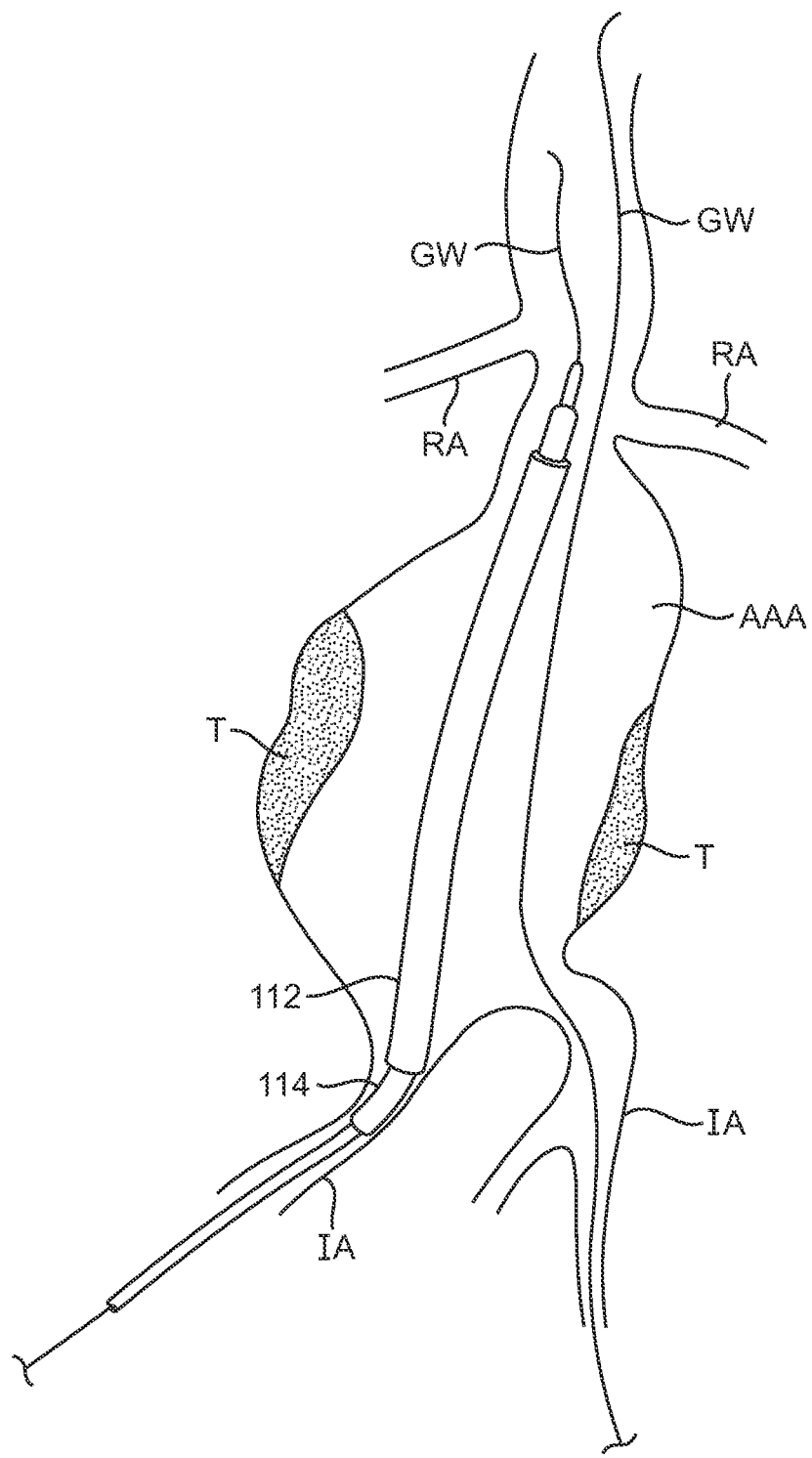
Figure 7C:
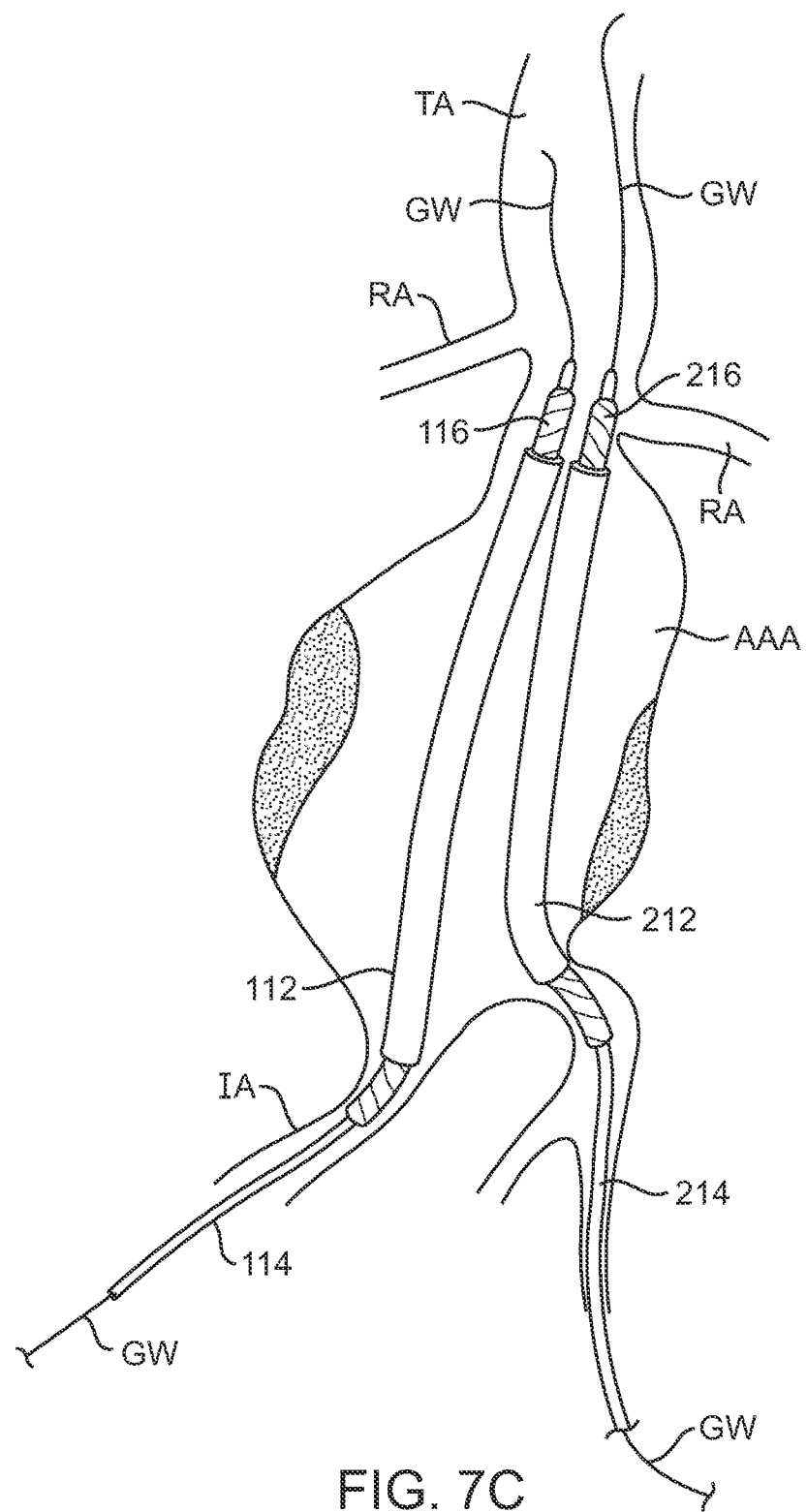
Figure 7D:
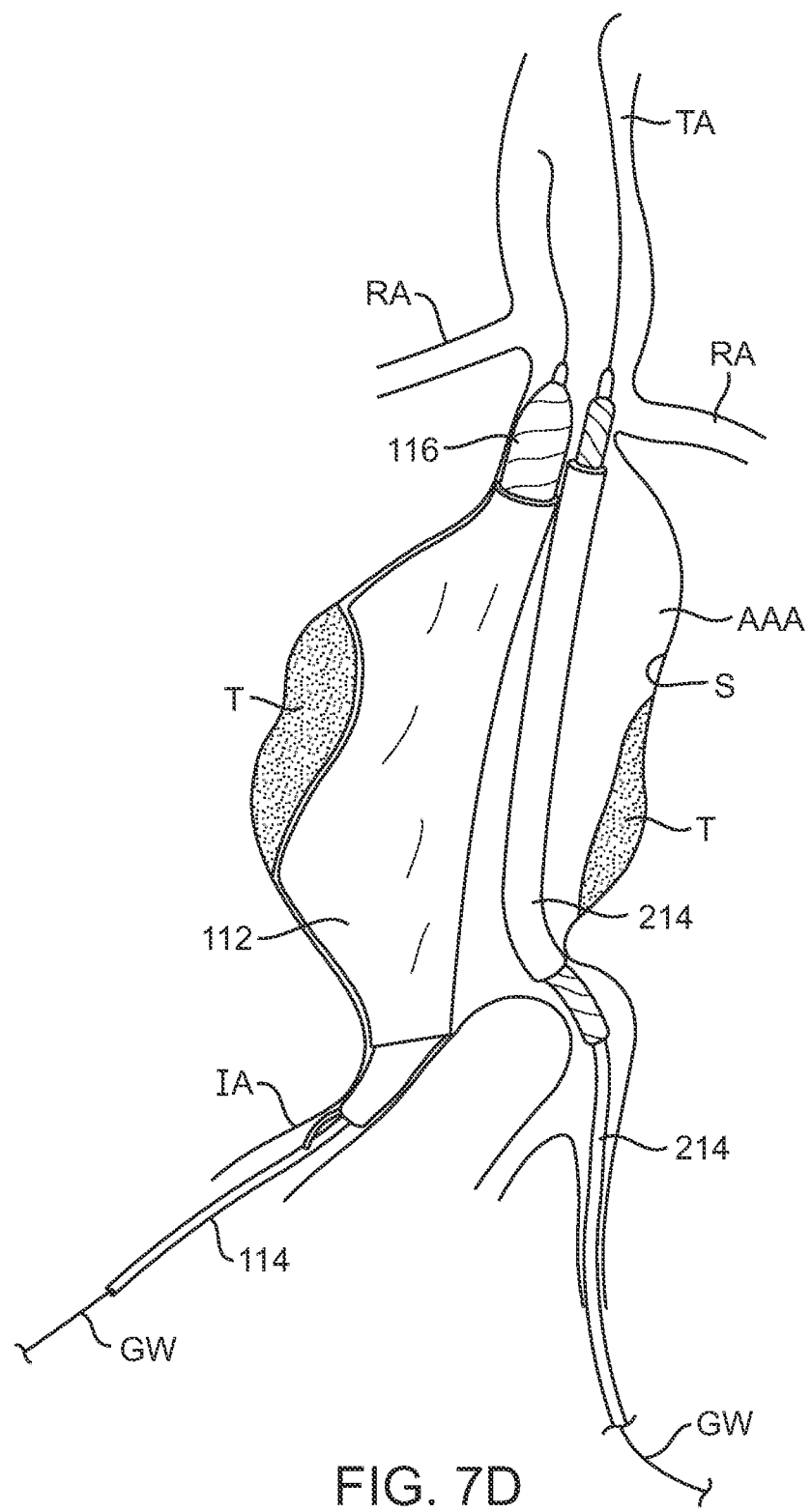
Figure 7E:
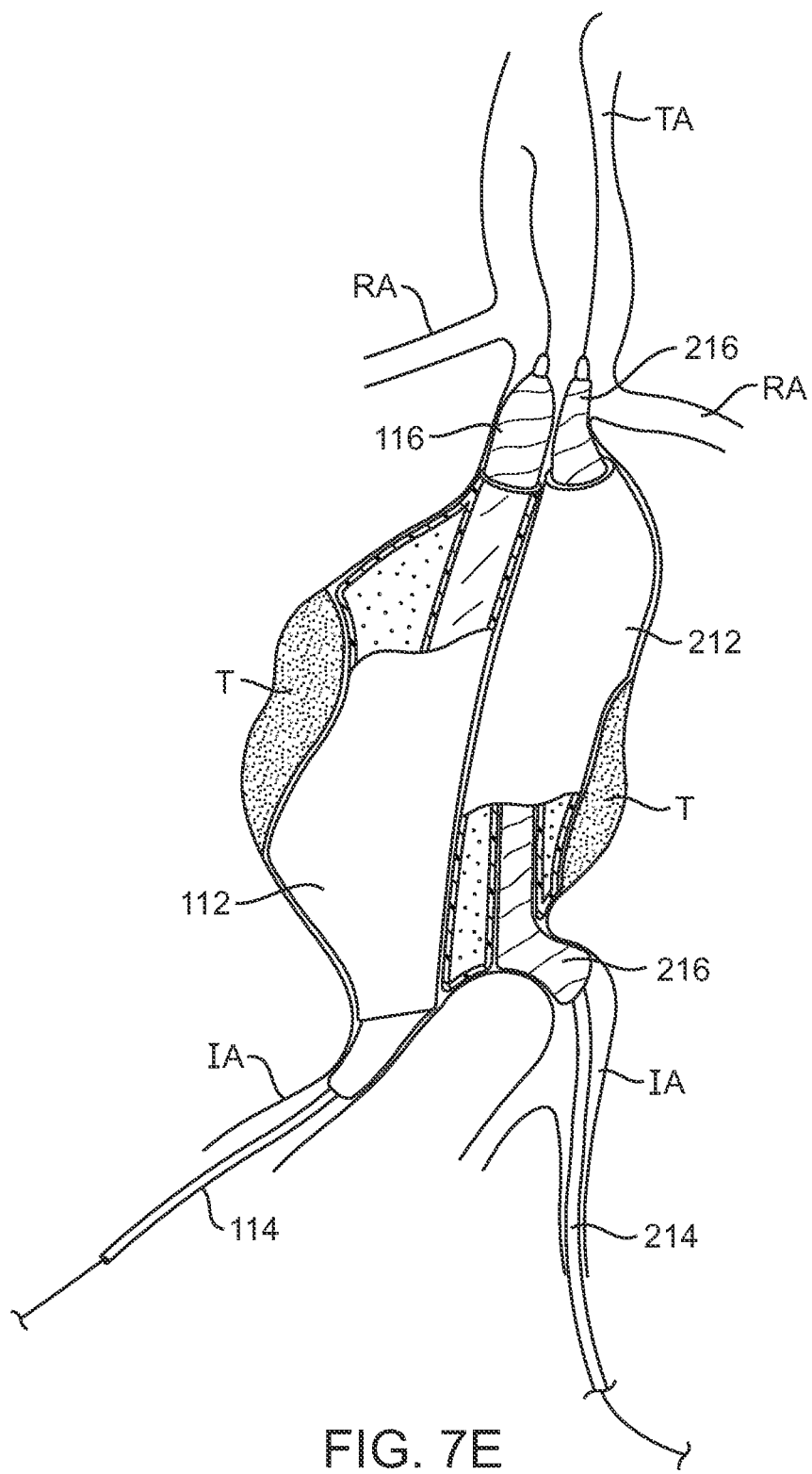

In treating an infrarenal abdominal aortic aneurysm using the pair of filling structures 112 and 212 illustrated in FIG. 6, a pair of guidewires (GW) will first be introduced, one from each of the iliac arteries (IA). As illustrated in FIG. 7A. The first delivery catheter 114 will then be positioned over one of the guidewires to position the double-walled filling structure 112 across the aortic aneurysm (AAA), as illustrated in FIG. 7B. The second delivery catheter 214 is then delivered over the other guidewire (GW) to position the second filling structure 212 adjacent to the first structure 112 within the aneurysm (AAA), as illustrated in FIG. 7C. Typically, one of the filling structures and associated balloons will be expanded first, followed by the other of the filling structures and balloon, as illustrated in FIG. 7D where the filling structure 112 and balloon 116 are inflated to fill generally half of the aneurismal volume, as illustrated in FIG. 7D. Filling can generally be carried out as described above with the one filling structure embodiment, except of course that the filling structure 112 will be expanded to occupy only about one-half of the aneurismal volume. After the first filling structure 112 has been filled, the second filling structure 212 may be filled, as illustrated in FIG. 7E. In other protocols the two filling structures may be filled simultaneously. The upper ends of the balloons 116 and 216 will conform the tubular lumens of the filling structures against the walls of the aorta as well as against each other, while the lower ends of the balloons 116 and 216 will conform the tubular lumens into the respective iliac (IA).

Figure 7F:
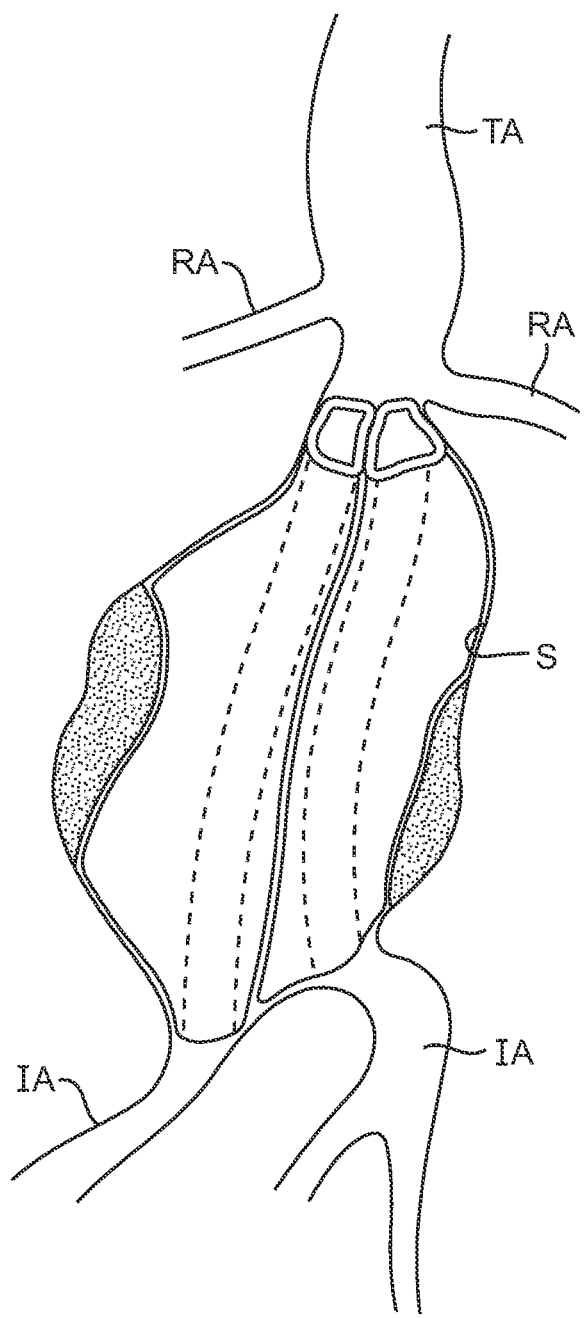

After filling the filling structures 112 and 212 as illustrated in FIG. 7E, the filling materials or medium will be cured or otherwise hardened, and the delivery catheters 114 and 214 removed, respectively. The hardened filling structures will then provide a pair of tubular lumens opening from the aorta beneath the beneath the renal arteries to the right and left iliac arteries, as shown in broken line in FIG. 7. The ability of the filling structures 112 and 212 to conform to the inner surface (S) of the aneurysm, as shown in FIG. 7F, helps the structures to remain immobilized within the aneurysm with little or no migration. Immobilization of the filling structures 112 and 114 may be further enhanced by providing any of the surface features described above in connection with the embodiments of FIG. 2.

As with the single filling structure embodiments described previously, the double filling structure embodiments will include at least one separate scaffold deployed within each of the tubular blood flow lumens. The scaffolds will generally be stent-like or graft-like vascular structures and will be deployed within the tubular lumens using balloon or other expansion catheters (in the case of malleable or balloon-expandable scaffolds) or using constraining sheaths (in the case of self-expanding scaffolds).

Figure 7G:
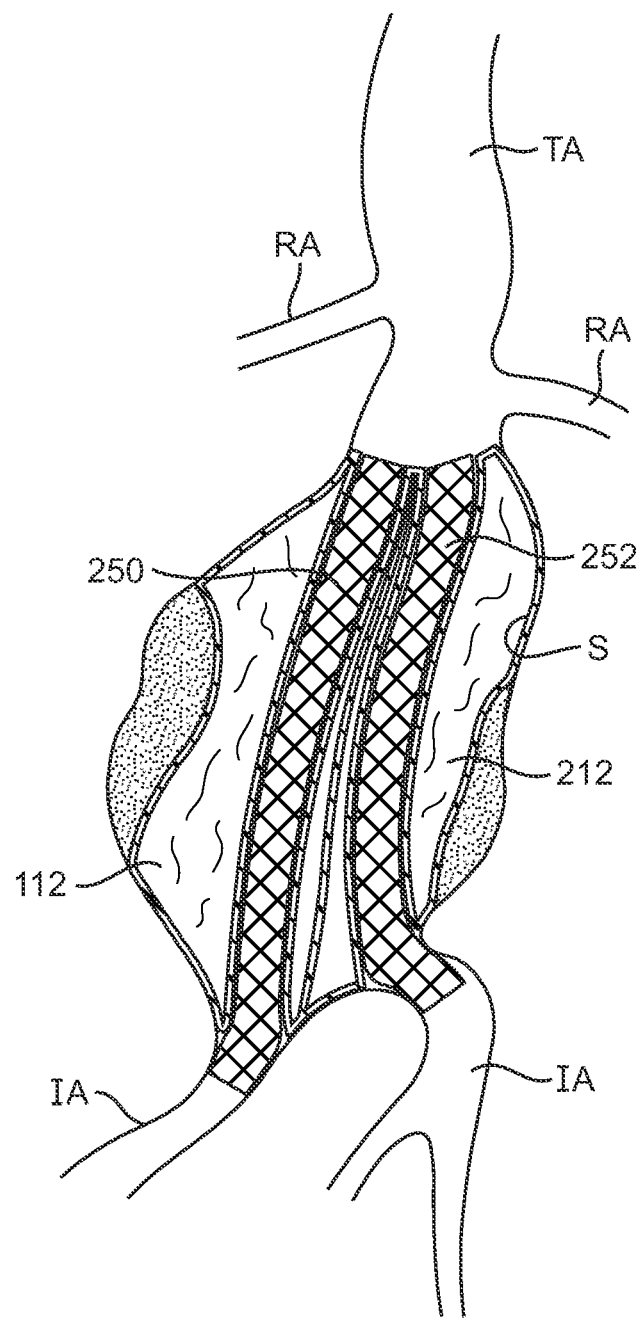
FIGS. 7G-7J illustrate the placement of scaffolds into the adjacent tubular lumens of the two filling structures of the prostheses of FIGS. 7A-7F.

Referring in particular to FIG. 7G, the first scaffold 250 may be placed in the tubular lumen of the first filling structure 112 while a second scaffold 252 may be placed in the tubular lumen of the second filling structure 212. As illustrated, the scaffolds are stent-like structures which extend into the iliac arteries IA at the lower end of the filling structures.

Figures 1, 2, 7H:
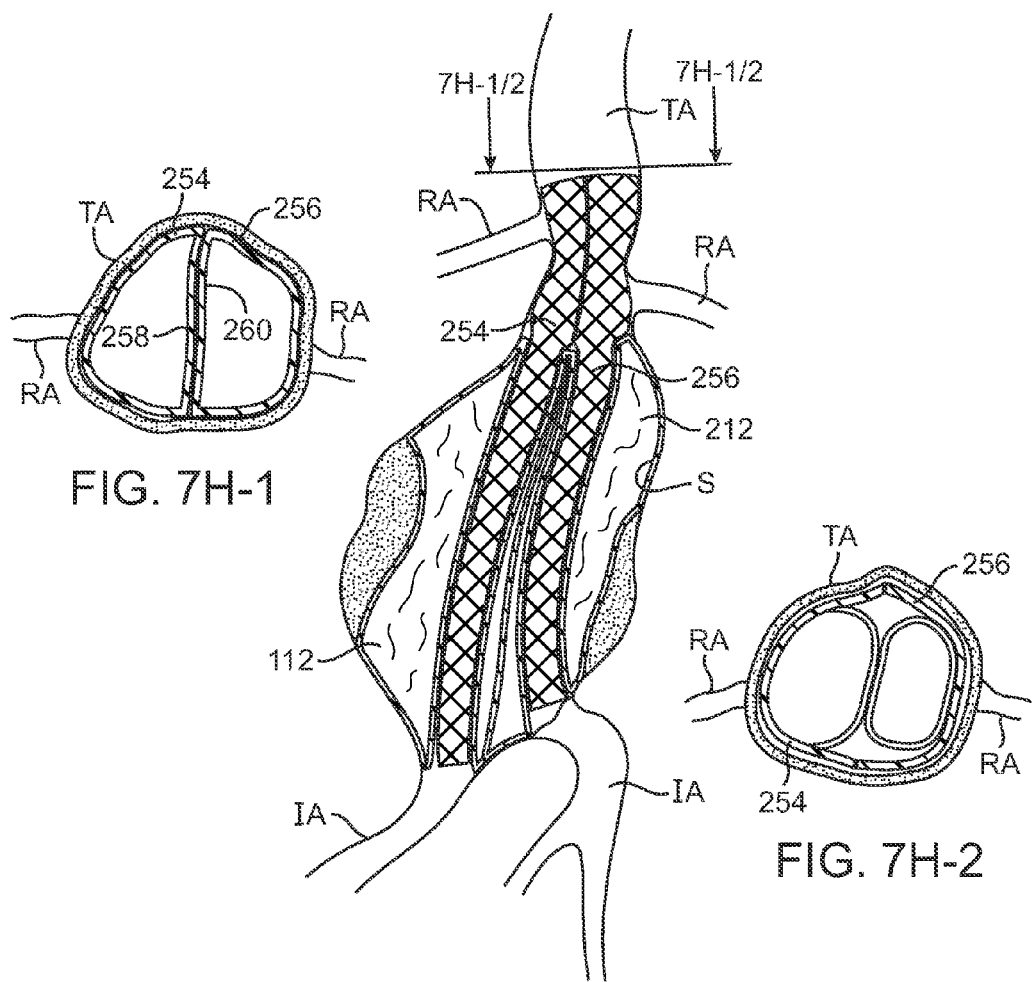

Referring now to FIG. 7H, first and second scaffolds 254 and 256 may extend upwardly on the aortic side of the first and second filling structures 112 and 212. When the separate stent or other scaffold structures extend into the thoracic aorta TA, it will usually be desirable that they be expanded so that they conform to each other along a plane or region of contact. For example, as shown in FIG. 7H-1, the upper ends of the scaffolds 254 and 256 may be formed preferentially to have D-shaped cross-sections when expanded. Thus, flat faces 258 and 260 will engage each other with the remaining portion of the stent conforming to the inner wall of the aorta. In this way, most of the cross-sectional area of the aorta will be covered with the stent, thus enhancing blood flow through the filling structures. Alternatively, as shown in FIG. 7H-2, the upper regions of the scaffolds 254 and 256 may be cut or otherwise modified to form open C-shaped cross-sections. In such cases, the expanded scaffolds can be arranged so that the C-shaped regions engage each other to form a continuous ring structure about the inner wall of the aorta. The open C-shaped regions will transition into a tubular region as the scaffolds enter the tubular lumens of the filling structures 112 and 212. In either of these embodiments, the scaffolds 254 and 256 may be partially or fully covered with a membrane or graft material, as described above in connection with other embodiments, particularly where such coverings extend partially or fully over the portion of the scaffold that extends into the adjacent blood vessel.

Figure 7I:
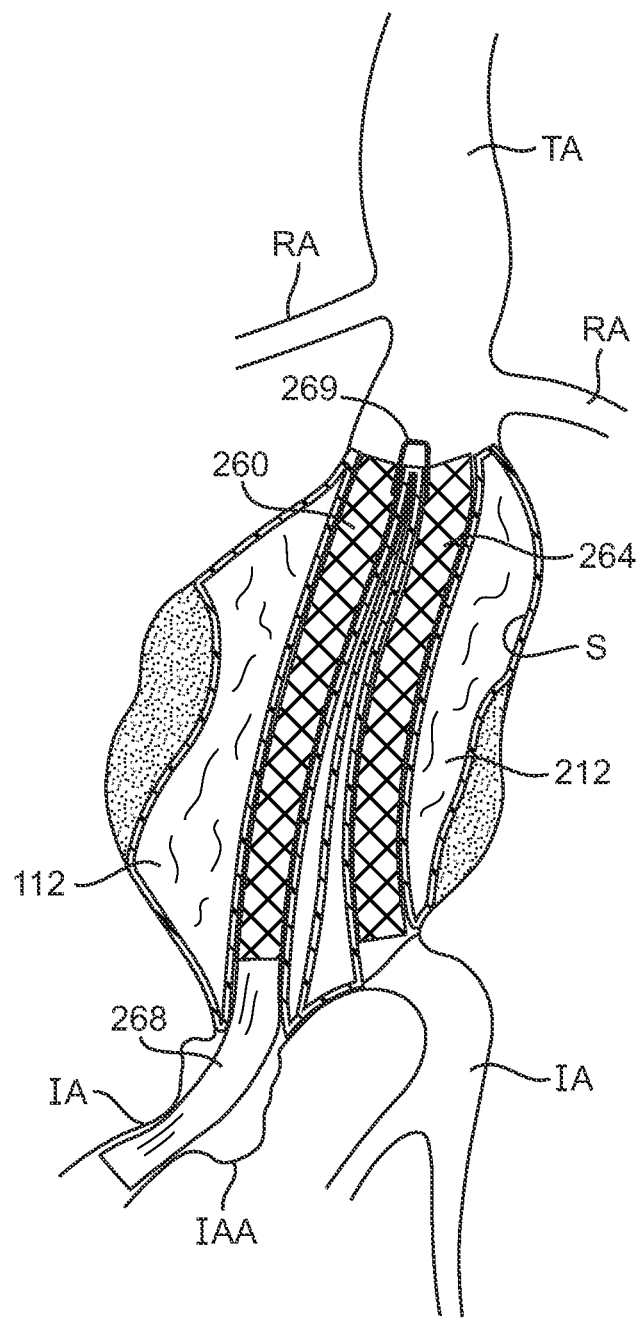

Referring now to FIG. 7I, scaffolds 260 and 264 may be implanted into the tubular lumens of the first filling structure 112 and second filling structure 212, respectively. The scaffold 260 includes an extension 268 at its lower end which is covered with a membrane or other material to form a graft region within the scaffold. This graft region 268 passes through an aneurysmal region within the iliac artery IA, thus allowing the structure to treat the iliac aneurysm as well as the aortic aneurysm. Optionally, a clip 269 or other fastening device, link, or tether, could be provided to connect the upper ends of the scaffolds 260 and 264 in the filling structures 112 and 212. By attaching the ends of the scaffolds, the distal ends of the filling structures will be stabilized and the risk of scaffold migration will be reduced.

Figure 7J:
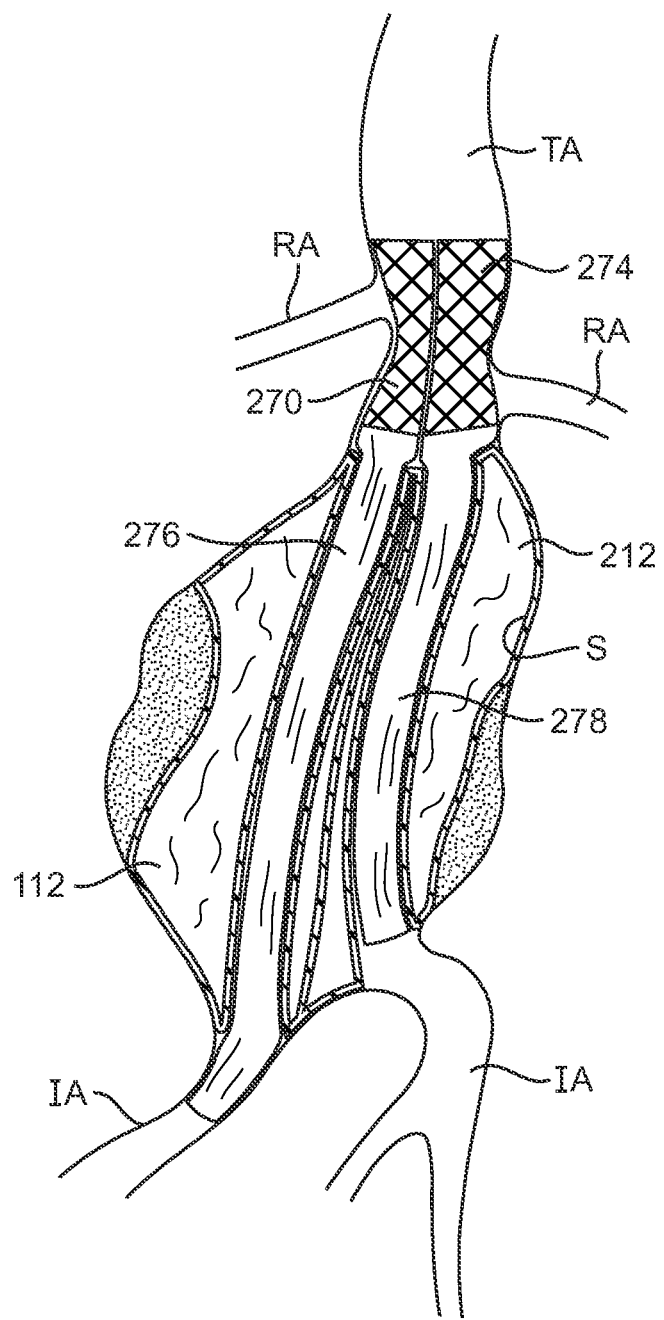

As shown in FIG. 7J, a first scaffold 270 and second scaffold 274 are placed in the first filling structure and second filling structure 112 and 212, respectively. The scaffold 270 has a membrane covering as metal frame through the entire length of the tubular lumen of the filling structure. In addition, the covered structure extends into the iliac artery. The portion of the first scaffold 270 extending into the aorta, however, is not covered to allow blood flows through the open mesh region of the metal frame. Similarly, the second scaffold 274 has an open mesh region in the aorta and a covered, graft-like region passing through the tubular lumen of the second filling structure 212. The second scaffold 274, however, does not extend into the iliac artery IA.

Various modifications of the protocols described above will be within the scope of the present invention. For example, while the scaffolds have been shown as being delivered after deployment of the filling structure(s), it will also be possible to deliver the scaffolds simultaneously with or prior to deployment of the filling structures. For example, the scaffolds could be delivered on the same delivery catheter(s) used to deliver and/or shape the filling structures. The scaffolds could then be expanded at the same time as filling the filling structure or even prior to filling the filling structure.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A system for treating an aneurysm in a blood vessel, said system comprising:
   at least a first double-walled filling structure having an outer wall and an inner wall, wherein said double-walled filling structure is adapted to be filled with a hardenable fluid filling medium so that when the first filling structure is deployed across the aneurysm, the outer wall conforms to the inside surface of the aneurysm across the aneurysm and the inner wall forms a first generally tubular lumen to provide a path for blood flow across the aneurysm such that blood flow is in direct contact with the inner wall along the first generally tubular lumen;
   at least a first scaffold separate from the first double-walled filling structure which can be expanded within at least a portion of the first tubular lumen of the filling structure;
   a second double-walled filling structure having an outer wall and an inner wall, wherein said second double-walled filling structure is adapted to be placed adjacent to the first double-walled filling structure in the aneurysm and to be filled with a hardenable fluid filling medium so that when the second filling structure is deployed across the aneurysm, the outer wall conforms to the inside surface of the aneurysm across the aneurysm and to the first double-walled filling structure and forms a second generally tubular lumen to provide a path for blood flow across the aneurysm such that blood flow is in direct contact with the inner wall along the second generally tubular lumen; and
   at least a second scaffold separate from the first scaffold and the double-walled filling structures which can be expanded within at least a portion of the second tubular lumen of the second double-walled filling structure.

2. A system as in claim 1, wherein the first scaffold extends over substantially an entire length of the first generally tubular lumen extending through the first double-walled filling structure.

3. A system as in claim 1, wherein the first scaffold is adapted to extend outwardly from at least one end of the first generally tubular lumen into the adjacent blood vessel.

4. A system as in claim 1, further comprising at least two scaffolds for placing in the first generally tubular lumen, wherein the at least two scaffolds are separate from the first filing structure.

5. A system as in claim 4, wherein the at least two scaffolds are adapted to be placed in series.

6. A system as in claim 1, wherein the first scaffold is malleable and adapted to be balloon expanded from a narrow diameter configuration to a deployed configuration.

7. A system as in claim 1, wherein substantially the entire first double-walled filling structure is formed from a compliant material.

8. A system as in claim 1, wherein at least a portion of an exterior surface of the first double-walled filling structure is modified to enhance sealing or tissue ingrowth.

9. A system as in claim 1, further comprising a first delivery catheter having an expandable tubular support which can be positioned within the first generally tubular lumen to carry the first double-walled filling structure.

10. A system as in claim 9, wherein the expandable tubular support is adapted to extend upstream and downstream from the first double-walled filling structure so that tubular support aligns and conforms each end of the first double-walled filling structure with the blood vessel.

11. A system as in claim 9, wherein the tubular support comprises an inflatable support balloon having a non-compliant structure.

12. A system as in claim 11, wherein the tubular support comprises a mechanical structure expandable to one or more fixed diameters.

13. A system as in claim 1, wherein each of the first and second scaffold have an end, wherein respective ends of the first and second scaffolds are adapted to extend outwardly in parallel in at least one direction from their respective tubular lumens into the adjacent blood vessel.

14. A system as in claim 13, wherein said respective ends have complementary shapes that are adapted to together conform to the wall of the adjacent blood vessel.

15. A system as in claim 14, wherein said respective ends have mating D-shaped cross-sections.

16. A system as in claim 1, further comprising;
   a first delivery catheter having an expandable support which can be positioned within the tubular lumen of the first double-walled filling structure; and
   a second delivery catheter having an expandable support which can be positioned within the tubular lumen of the second double-walled filling structure.

17. A system as in claim 16, wherein the expandable support on each of the first and second delivery catheter is adapted to extend upstream and downstream from the respective double-walled filling structure so that the expandable support aligns and conforms each end of the respective double-walled filling structure with the iliac and aorta.

18. A system as in claim 16, wherein the expandable support on each delivery catheter comprises a mechanical structure expandable to one or more fixed diameter.

19. A system as in claim 1, further comprising a hardenable fluid filling medium including a flowable polymer which is curable in situ.

20. A system as in claim 1, wherein the hardenable fluid filling medium has a specific gravity in the range from 0.1 to 5 when hardened.

* * * * *